(12) United States Patent
Schuler et al.

(10) Patent No.: US 6,751,501 B1
(45) Date of Patent: Jun. 15, 2004

(54) METHOD AND APPARATUS FOR MYOCARDIAL CONTROL

(75) Inventors: Eleanor L. Schuler, Rio Rancho, NM (US); Dale L. Scott, Albuquerque, NM (US)

(73) Assignee: Science Medicus, Inc., Reno, NV (US)

( * ) Notice: Subject to any disclaimer, the term of this patent is extended or adjusted under 35 U.S.C. 154(b) by 0 days.

(21) Appl. No.: 09/483,310

(22) Filed: Jan. 14, 2000

Related U.S. Application Data

(63) Continuation-in-part of application No. PCT/US98/14751, filed on Jul. 17, 1998.
(60) Provisional application No. 60/052,881, filed on Jul. 17, 1997, provisional application No. 06/052,891, filed on Jul. 17, 1997, provisional application No. 60/079,514, filed on Mar. 26, 1998, provisional application No. 60/116,025, filed on Jan. 15, 1999, and provisional application No. 06/116,094, filed on Jan. 15, 1999.

(51) Int. Cl.[7] ................................................. A61N 1/36
(52) U.S. Cl. ............................................................ 607/4
(58) Field of Search ........................................ 607/4, 5

(56) References Cited

U.S. PATENT DOCUMENTS

| | | | |
|---|---|---|---|
| 3,716,059 A | 2/1973 | Welborn et al. | 128/419 D |
| 4,419,998 A | 12/1983 | Heath | 128/639 |
| 4,637,397 A | 1/1987 | Jones et al. | 128/419 D |
| 4,735,206 A | 4/1988 | Hewson | 128/419 D |
| 4,895,169 A | 1/1990 | Heath | 128/798 |
| 4,928,674 A | 5/1990 | Halperin et al. | 128/30.2 |
| 4,955,381 A | 9/1990 | Way et al. | 128/640 |
| 5,012,814 A | 5/1991 | Mills et al. | 128/691 |
| 5,080,099 A | 1/1992 | Way et al. | 128/640 |
| 5,184,620 A | 2/1993 | Cudahy et al. | 128/639 |
| 5,224,476 A | 7/1993 | Ideker et al. | 128/419 D |
| 5,265,600 A | 11/1993 | Adams et al. | 607/4 |
| 5,284,135 A | 2/1994 | Lopin | 607/4 |
| 5,314,448 A | 5/1994 | Kroll et al. | 607/5 |
| 5,356,428 A | 10/1994 | Way | 607/142 |
| 5,366,485 A | 11/1994 | Kroll et al. | 607/5 |
| 5,366,497 A | 11/1994 | Ilvento et al. | 607/142 |
| 5,374,287 A | 12/1994 | Rubin | 607/131 |
| 5,391,187 A | 2/1995 | Freeman | 607/5 |
| 5,417,713 A | 5/1995 | Cohen | 607/4 |
| 5,464,429 A | 11/1995 | Hedberg et al. | 607/4 |
| 5,476,502 A | 12/1995 | Rubin | 607/127 |
| 5,522,853 A | 6/1996 | Kroll | 607/5 |
| 5,571,142 A | 11/1996 | Brown et al. | 607/5 |
| 5,593,428 A | 1/1997 | Jamshidi | 607/10 |

OTHER PUBLICATIONS

"Multicenter Comparison of Truncated Biphasic Shocks and Standard Damped Sine Wave Monophasic Shocks for Transthoracic Ventricular Defibrillation" G. H. Bardy et al. *Circulation*, vol. 97, No. 10 Nov. 15, 1996. pp. 2507–2514.

*Primary Examiner*—Scott M. Getzow
(74) *Attorney, Agent, or Firm*—Barnes & Thornburg

(57) ABSTRACT

A monolithic device (10) for providing defibrillation, pacing, and cardiac paralysis of a heart. Various electronic waveforms are generated by the device and are selected for the type of control required. Defibrillation and pacing of a human heart from outside the body employs defibrillation circuitry having an electromotive force of less than or equal to approximately 200 volts. Digital circuitry for generating direct current waveforms to the heart is employed.

8 Claims, 23 Drawing Sheets

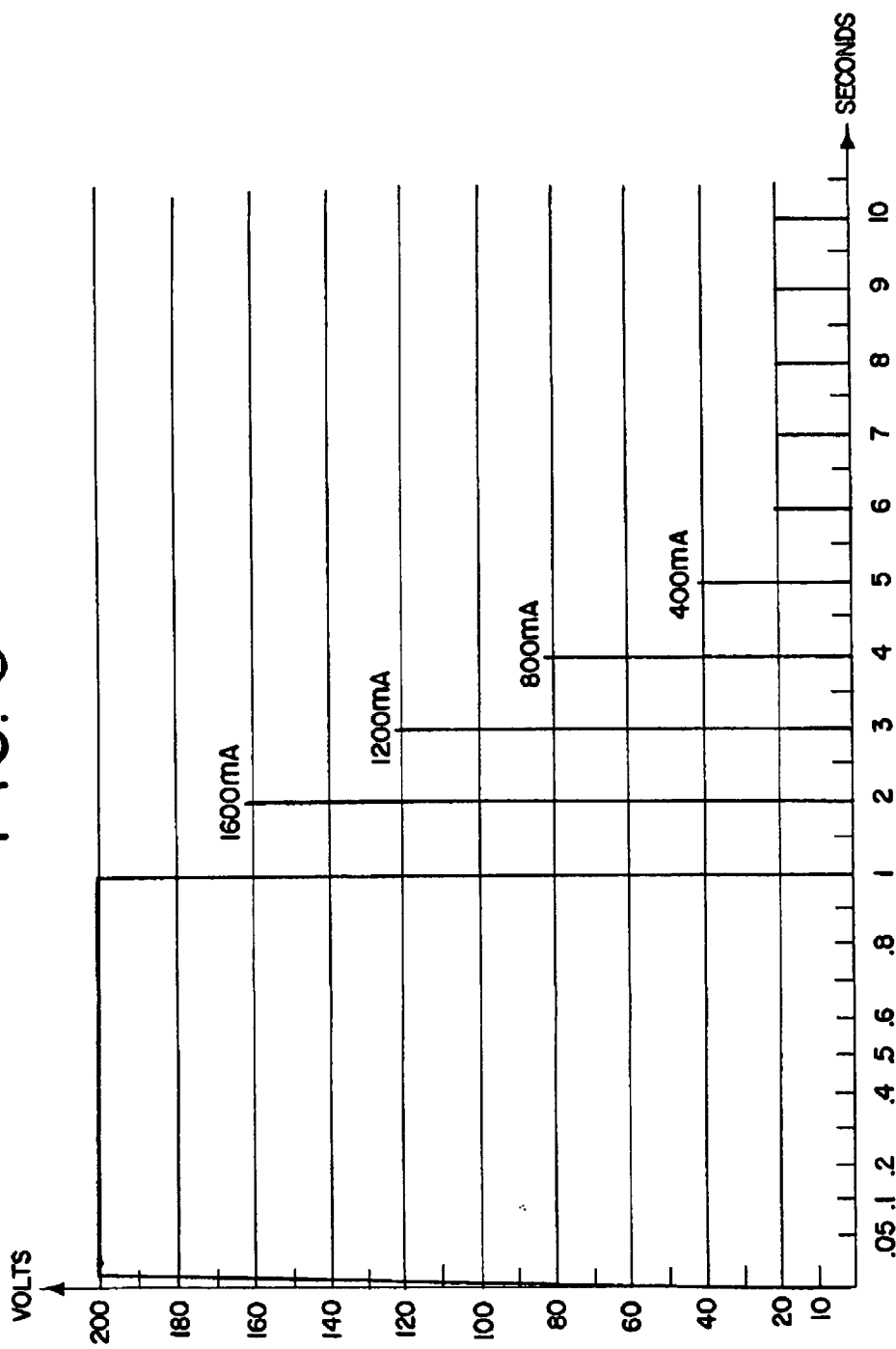

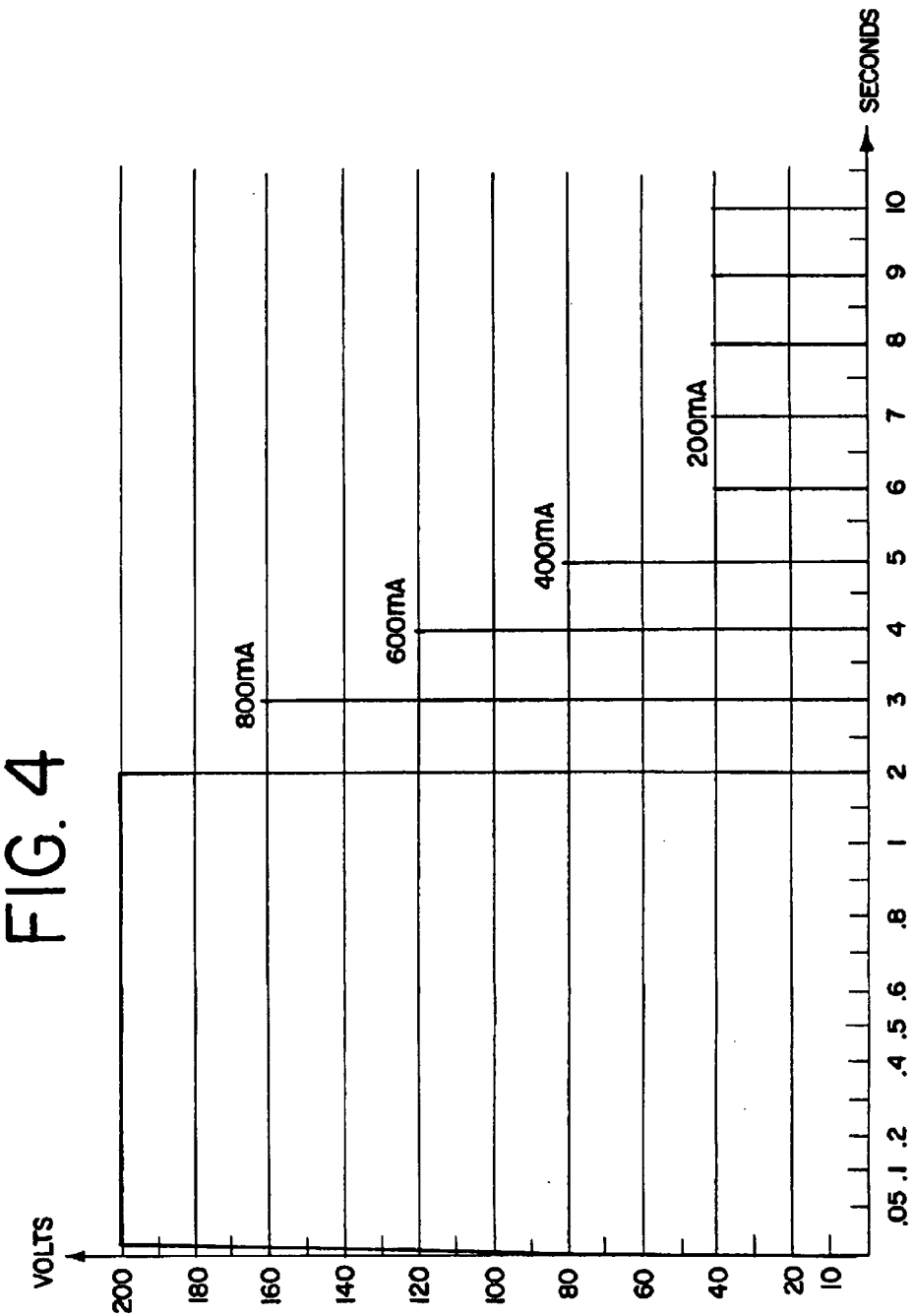

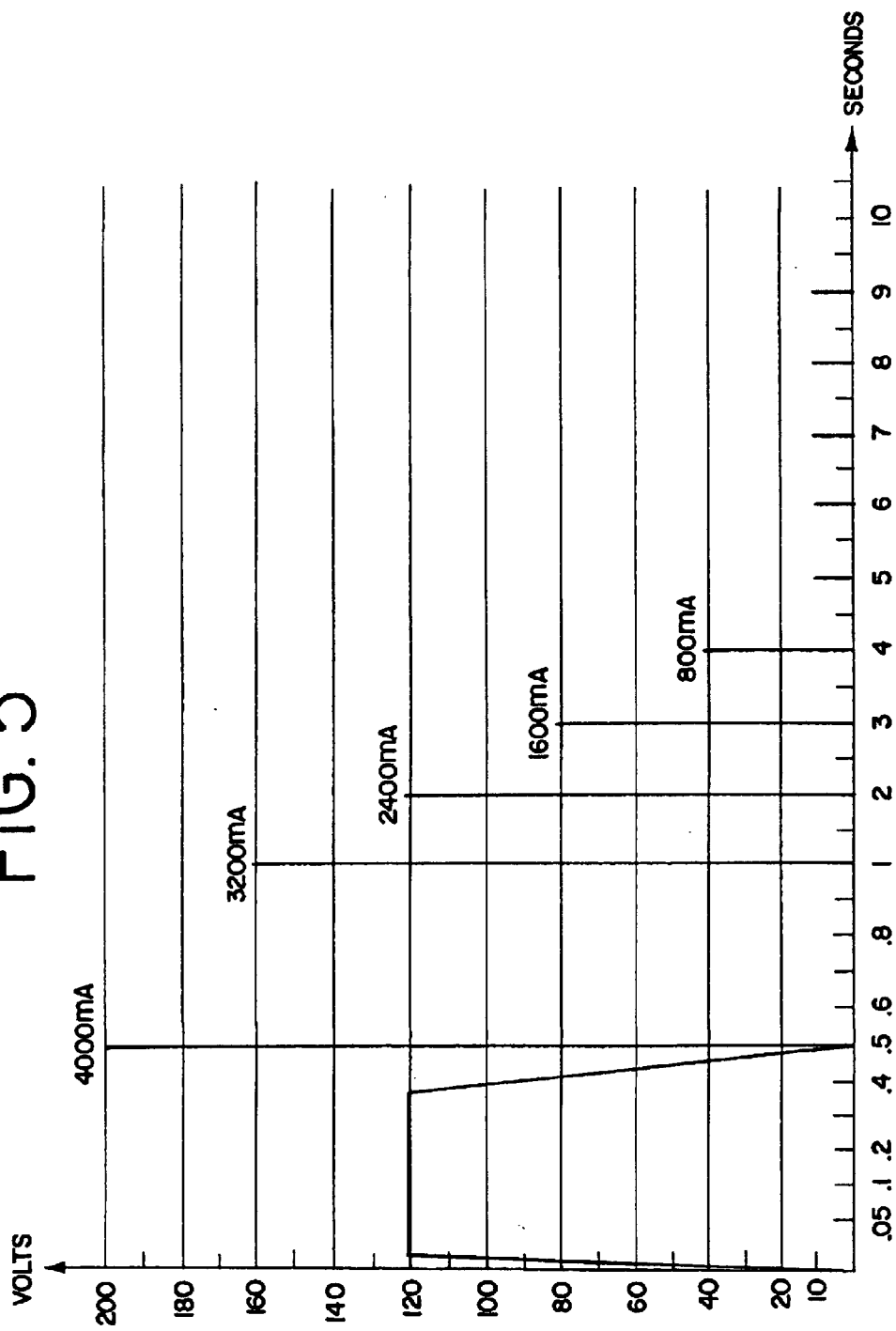

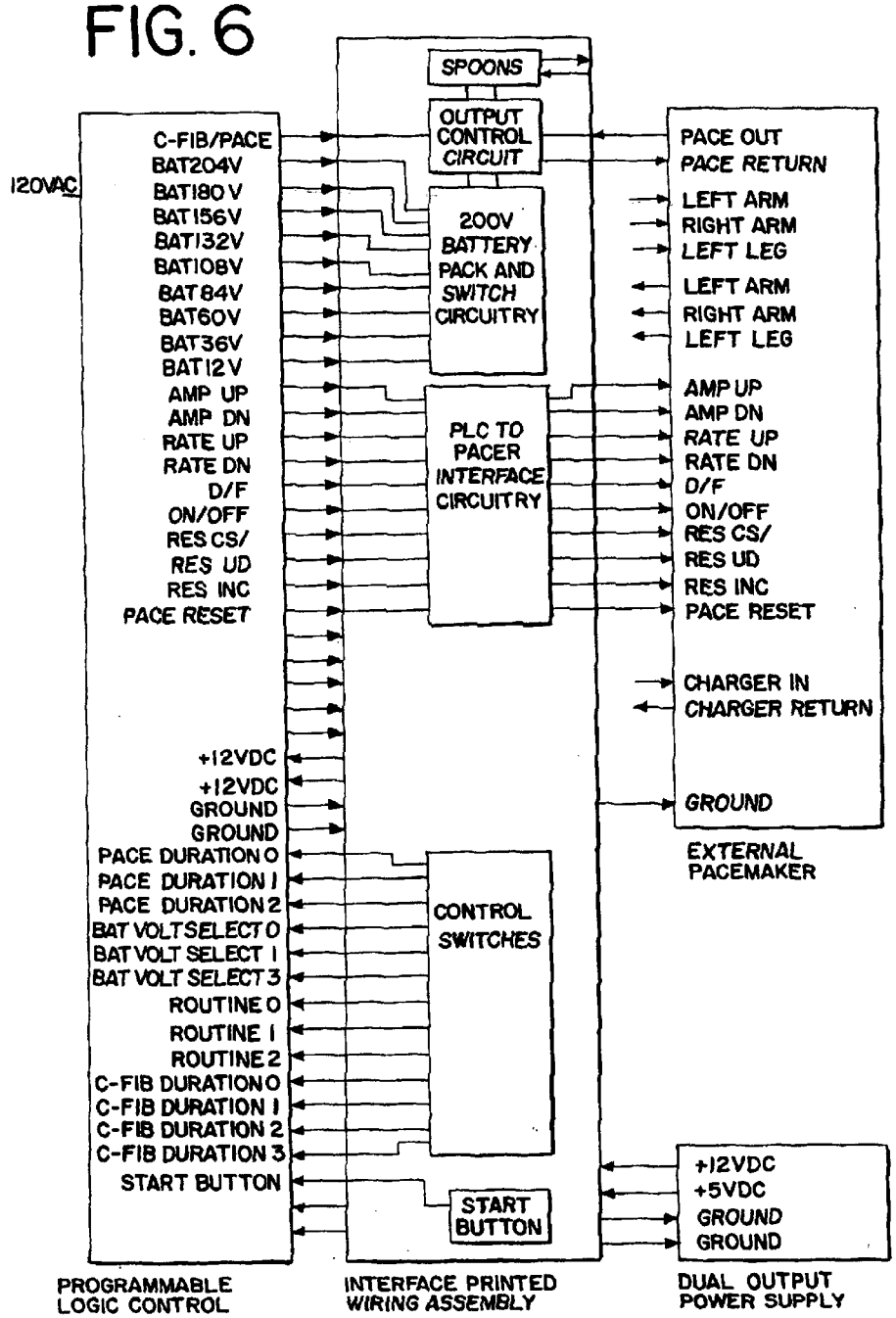

FIG. 7

| C-FIB DURATION SWITCH | |
|---|---|
| SWITCH SETTINGS | DURATION IN SEC |
| 0 | 0.5 |
| 1 | 1 |
| 2 | 1.5 |
| 3 | 2 |
| 4 | 2.5 |
| 5 | 3 |
| 6 | 3.5 |
| 7 | 4 |
| 8 | 4.5 |
| 9 | 5 |
| 10 | NOT USED |
| 11 | NOT USED |
| 12 | NOT USED |
| 13 | NOT USED |
| 14 | NOT USED |
| 15 | NOT USED |

| C-FIB AMPLITUDE SWITCH | HIGH VOLTAGE SWITCH | | |
|---|---|---|---|
| SWITCH SETTINGS | (ZERO) | (ONE) | (TWO) |
| 0 | 4 | 68 | 132 |
| 1 | 8 | 72 | 136 |
| 2 | 12 | 76 | 140 |
| 3 | 16 | 80 | 144 |
| 4 | 20 | 84 | 148 |
| 5 | 24 | 88 | 152 |
| 6 | 28 | 92 | 156 |
| 7 | 32 | 96 | 160 |
| 8 | 36 | 100 | 164 |
| 9 | 40 | 104 | 168 |
| 10 | 44 | 108 | 172 |
| 11 | 48 | 112 | 176 |
| 12 | 52 | 116 | 180 |
| 13 | 56 | 120 | 184 |
| 14 | 60 | 124 | 188 |
| 15 | 64 | 128 | 192 |

| PACER DURATION SWITCH | | |
|---|---|---|
| SWITCH SETTINGS | SELECTION OF K OHMS | PULSE DURATION |
| 0 | 100 | 0.1 |
| 1 | 95 | 0.095 |
| 2 | 90 | 0.09 |
| 3 | 85 | 0.085 |
| 4 | 80 | 0.08 |
| 5 | 75 | 0.075 |
| 6 | 70 | 0.07 |
| 7 | 65 | 0.065 |
| 8 | 60 | 0.06 |
| 9 | 55 | 0.055 |
| 10 | 50 | 0.05 |
| 11 | 45 | 0.045 |
| 12 | 40 | 0.04 |
| 13 | 35 | 0.035 |
| 14 | 30 | 0.03 |
| 15 | 25 | 0.025 |

| ROUTINE SWITCH | |
|---|---|
| SWITCH SETTING | ROUTINE |
| 0 | C-FIB PULSE AND 5 TIME CONSTANTS DECREMENT OF PACER AMPLITUDE |
| 1 | C-FIB PULSE AND STEADY STATE PACER AMPLITUDE |
| 2 | BIPHASIC C-FIB PULSE AND 5 TIME CONSTANTS DECREMENT OF PACER AMPLITUDE |
| 3 | BIPHASIC C-FIB PULSE AND STEADY STATE PACER AMPLITUDE |
| 4 | STEADY STATE PACING WITH NO C-FIB PULSE |
| 5 | C-FIB PULSE WITH NO PACING |
| 6 | MULTI-PHASIC C-FIB PULSE AND 5 TIME CONSTANTS DECREMENT OF PACER AMPLITUDE |
| 7 | MULTI-PHASIC C-FIB PULSE AND STEADY STATE PACER AMPLITUDE |
| 8 | NOT USED |
| 9 | NOT USED |
| 10 | NOT USED |
| 11 | NOT USED |
| 12 | NOT USED |
| 13 | NOT USED |
| 14 | NOT USED |
| 15 | BSM MODE |

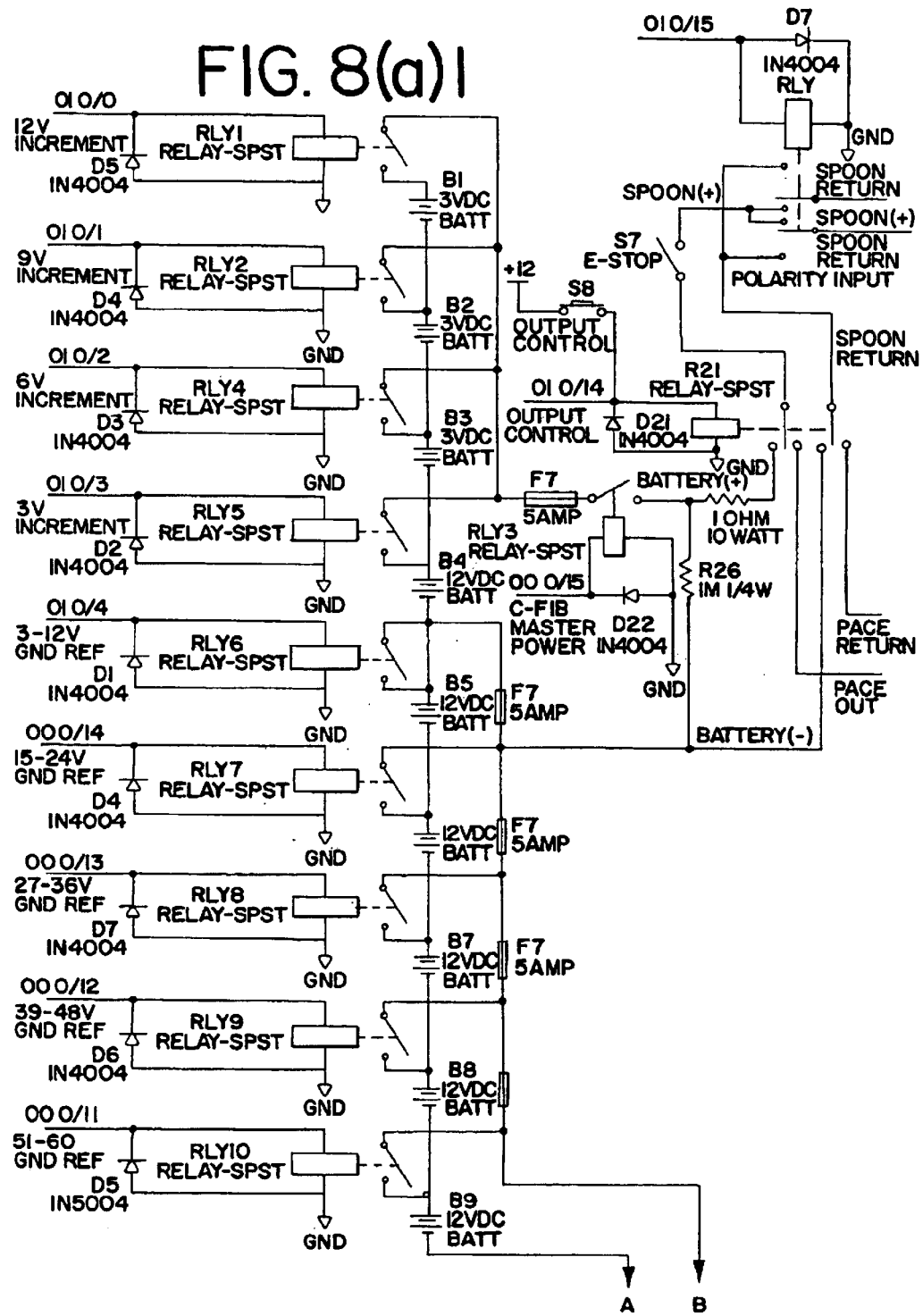

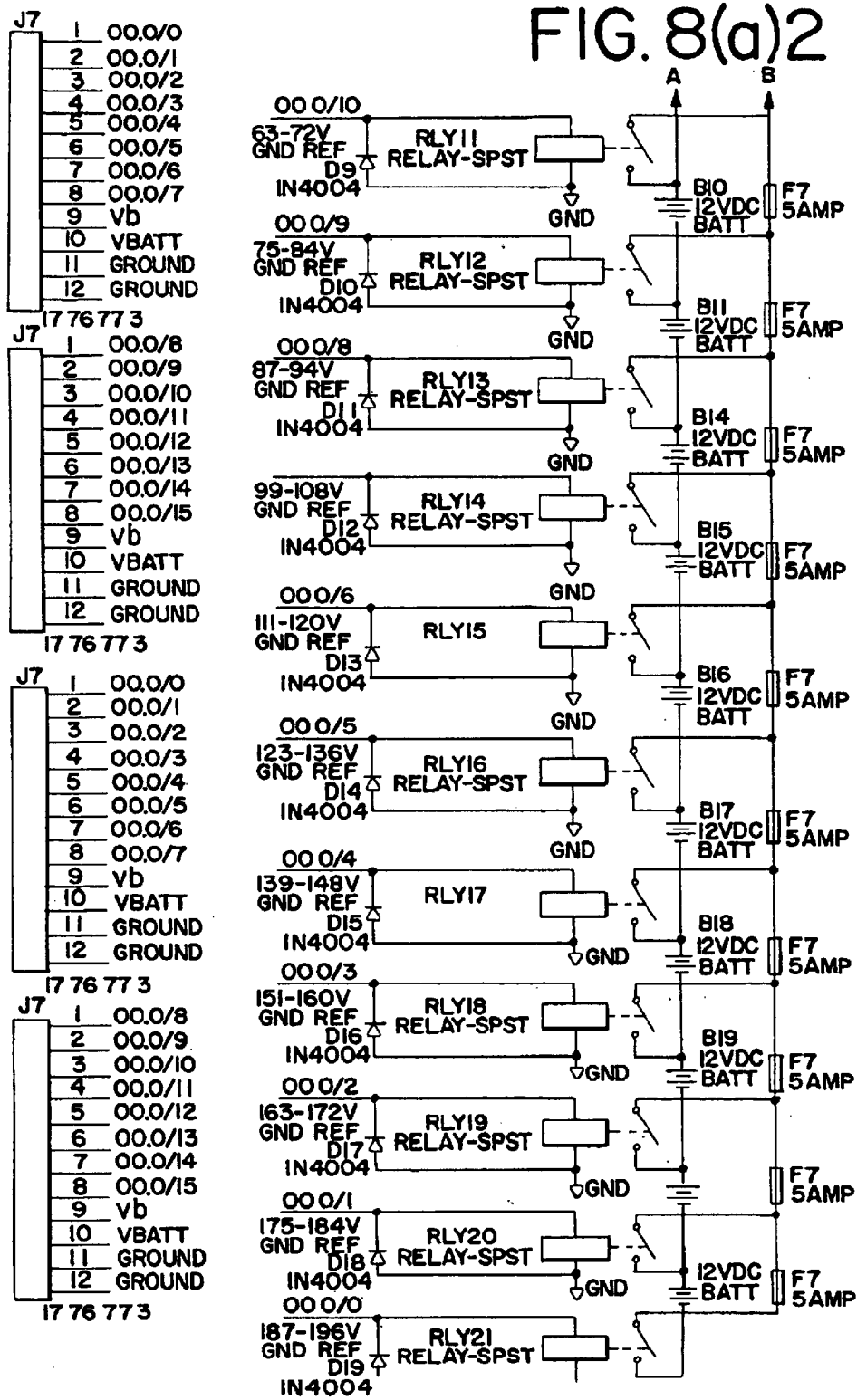

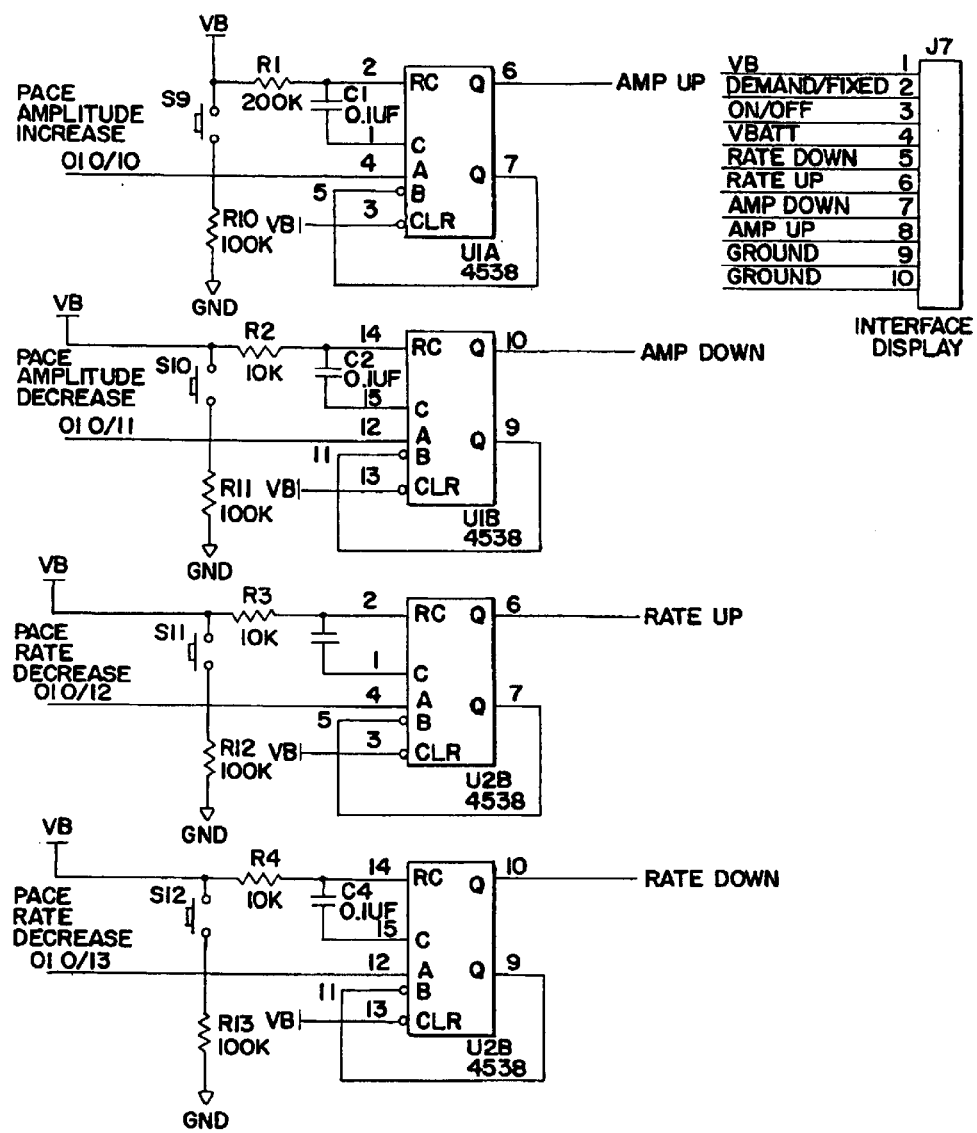
FIG.8(b)1

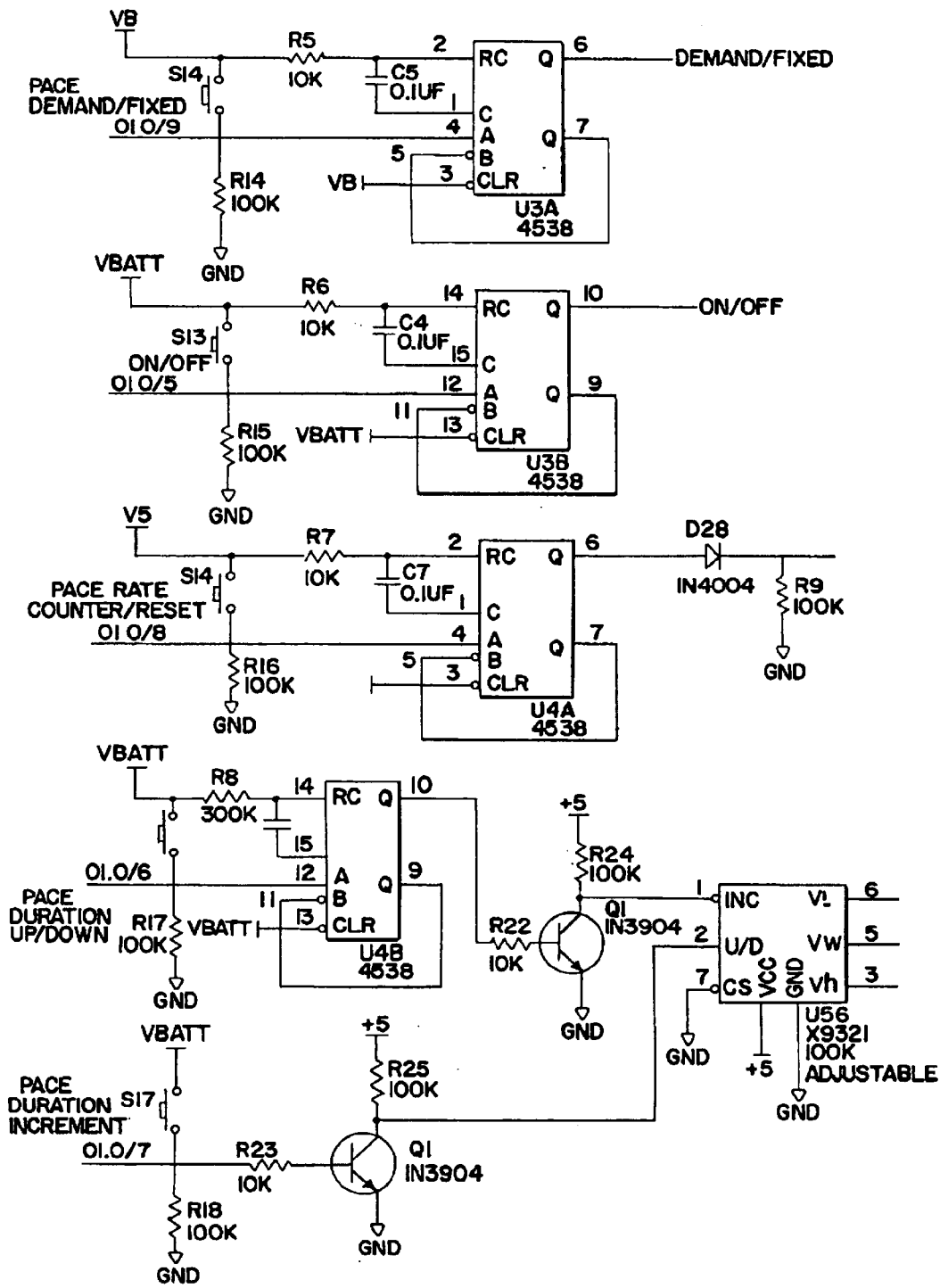
FIG. 8(b)2

FIG. 9

R-WAVE

| J1 PIN | DESCRIPTION |
|---|---|
| 1 | VB |
| 2 | DEMAND/FIXED-(SWITCH VB) |
| 3 | ON/OFF-(SWITCH V BATT) |
| 4 | V BATT |
| 5 | RATE DOWN-(SWITCH VB) |
| 6 | RATE UP-(SWITCH VB) |
| 7 | AMP DOWN-(SWITCH VB) |
| 8 | AMP UP-(SWITCH VB) |
| 9 | GROUND |
| 10 | GROUND |

| J2 PIN | DESCRIPTION |
|---|---|
| 1 | RATE-LSB PIN |
| 2 | RATE- |
| 3 | RATE- |
| 4 | RATE-MSB |
| 5 | AMP-LSB |
| 6 | AMP- |
| 7 | AMP- |
| 8 | AMP-MSB |
| 9 | GROUND |
| 10 | VB |
| 11 | GROUND |
| 12 | LOW BATTERY (FROM OP-AMP) |
| 13 | PACE/BLANK (FROM OP-SHOT) |
| 14 | FIX/DEM (INPUT TO 06) |
| 15 | VBATT |
| 16 | CHARGE INDICATOR (J3 PIN 5) |
| 17 | OPEN |
| 18 | OPEN |
| 19 | OPEN |
| 20 | OPEN |

| J3 PIN | DESCRIPTION |
|---|---|
| 1 | V BATT |
| 2 | GROUND |
| 3 | 33 uF GROUND |
| 4 | 70 VOLT FROM COIL |
| 5 | CHARGE INDICATOR |

| J4 PIN | DESCRIPTION |
|---|---|
| 1 | RA OUT |
| 2 | LA OUT |
| 3 | LL OUT |
| 4 | OPEN |

| J5 PIN | DESCRIPTION |
|---|---|
| 1 | RA IN |
| 2 | LA IN |
| 3 | LL IN |
| 4 | |
| 5 | PACE OUT(-) |
| 6 | PACE OUT(+) |

DISPLAY

| PIN | DESCRIPTION |
|---|---|
| 1 | RATE-LSP |
| 2 | RATE- |
| 3 | RATE- |
| 4 | RATE-MSB |
| 5 | AMP-LSB |
| 6 | AMP- |
| 7 | AMP- |
| 8 | AMP-MSB |
| 9 | GROUND |
| 10 | VB |
| 11 | GROUND |
| 12 | LOW BATTERY (OUTPUT TO LED) |
| 13 | PACE/BLANK (OUTPUT TO LED) |
| 14 | FIX/DEM (OUTPUT TO LED) |
| 15 | VBATT |
| 16 | CHARGE INDICATOR (J3 PIN 5) |
| 17 | GROUND |
| 18 | GROUND |
| 19 | GROUND |
| 20 | GROUND |

POWER

| PIN | DESCRIPTION |
|---|---|
| 1 | VBATT |
| 2 | GROUND |
| 3 | VB |
| 4 | 70 VOLT FROM COIL |
| 5 | CHARGE INDICATOR |

| J6 PIN | DESCRIPTION |
|---|---|
| 1 | VBATT(+) |
| 2 | GROUND |

| J7 PIN | DESCRIPTION |
|---|---|
| 1 | RAIN |
| 2 | GROUND |

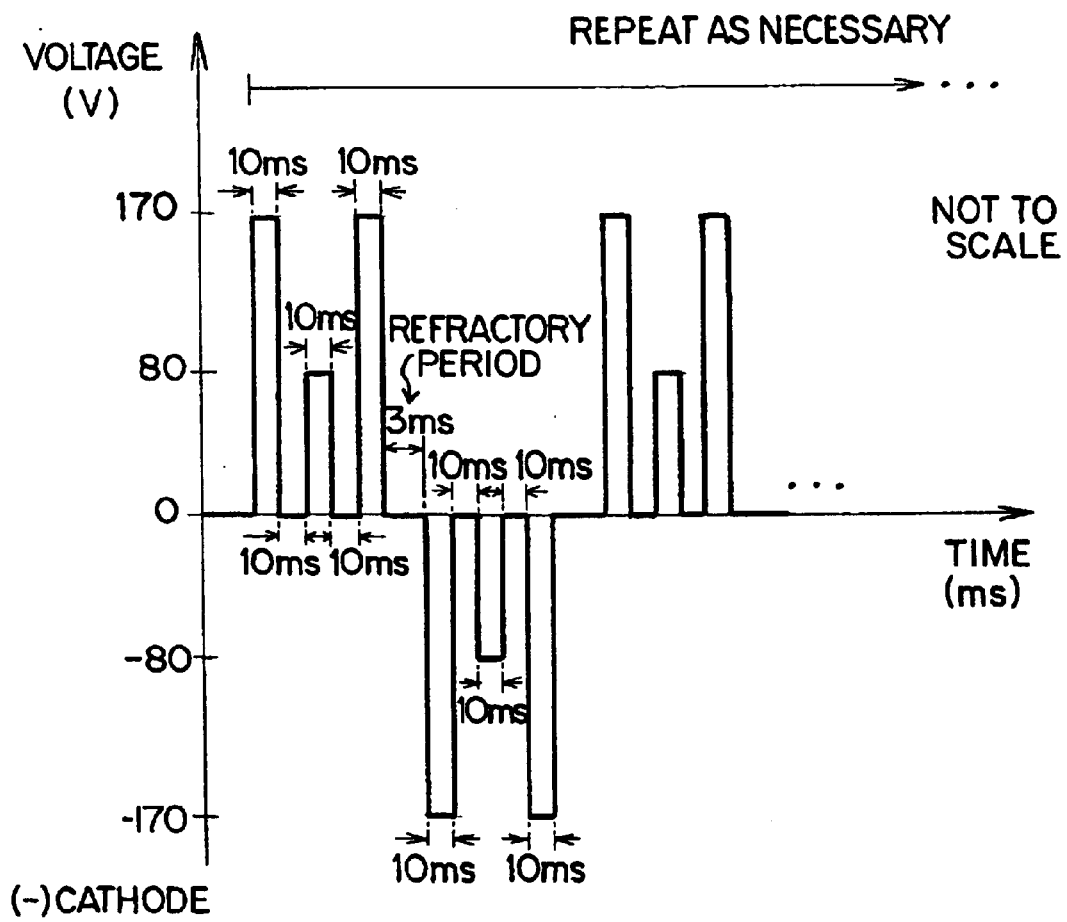

METHOD AND APPARATUS FOR MYOCARDIAL CONTROL

CROSS-REFERENCE TO RELATED APPLICATIONS

This is a continuation-in-part of International Application PCT/US98/14751, with an international filing date of Jul. 17, 1998, now abandoned, entitled "Defibrillator/Pacemaker," which claims priority to U.S. Provisional Patent Application Serial No. 60/052,881, entitled "System for Control of Cardiac Arrhythmia," filed on Jul. 17, 1997; U.S. Provisional Patent Application Serial No. 60/052,891, entitled "Method to Stop Fibrillating Human or Animal Hearth," filed on Jul. 17, 1997; and U.S. Provisional Patent Application Serial No. 60/079,514, entitled "Electronic Waveform and Generating Devices for Treating Cardiac Arrhythmia," filed on Mar. 26, 1998; and the specifications thereof are incorporated herein by reference.

This application also claims the benefit of the filing of U.S. Provisional Patent Application Serial No. 60/116,025, entitled "Electrical Waveforms for Myocardial Control," filed on Jan. 15, 1999, and U.S. Provisional Patent Application Serial No. 60/116,094, entitled "Cardiac Paralysis Device to Allow Surgical Treatment," filed on Jan. 15, 1999, and the specifications thereof are incorporated herein by reference.

BACKGROUND OF THE INVENTION

1. Field of the Invention (Technical Field)

The present invention relates to control of the heart, in particular defibrillation, pacing, and cardiac paralysis.

2. Background Art

Existing devices for treating cardiac arrhythmia require deployment of high voltages which can, and often do, cause injury to the patient. The present invention permits utilization of low voltages and greatly decrease the risk of further injury to the patient.

An arrhythmia is any abnormal electrical contraction of heart. Particular arrhythmias include: asystole—no beat at all or "flat-line" on monitor; bradycardia—slow beat, less than 60 beats per minute; tachycardia—fast beat, over 100 beats per minute; and fibrillation—life threatening chaotic heart action in which the heart twitches or quivers rapidly and is unable to pump efficiently.

During fibrillation, less blood is circulating and thus all systems of the human or animal body are at risk. The longer fibrillation continues unchecked the more likely death will occur. For every minute of fibrillation, a 10% reduction of life potential is subtracted, i.e., ten minutes results almost certain death. During fibrillation the electrical system of the heart is disorganized and erratic. The normal rhythmic beat is totally lost. Serious life threatening events begin to occur. Breathing becomes erratic and then stops as electrical failure begins. Shortly the inadequate circulation of blood causes organs and tissues to be oxygen starved and cell death begins. When brain and heart muscle oxygen starvation reach crisis points they begin to die and hence the entire body begins to die. At some point the heart fibrillations are not reversible and death of the human or animal occurs. It is important to stop fibrillation and to restart or regain the same level of heart contractions to oxygenate the entire body properly.

Fibrillation is currently typically treated by an electronic defibrillator which delivers a shock via two hand-held paddles. This process is familiar to those who view medical television shows and witness a shock so great that the entire body jumps. This shock is about 2,000 to 5,600 volts for external shocks and 310 to 750 volts for internal defibrillators. Repeated use of such large electrical shocks likely may damage the nervous system to such an extent that disabilities shall be present even if the patient lives. The popular conception is that a defibrillator "puts" a heart beat into a stopped heart. Actually, a defibrillator stops the quivering heart, after which, but not always, the heart may resume a slow beat (bradycardia). Paramedics then can use medications to speed up the heart and/or administer an emergency external pacemaker while transporting the victim to a hospital.

In the science of electromyography there is a graphical presentation of fibrillation on a visual monitor of a heart muscle being affected by a monophasic, biphasic or triphasic spike usually of 25 to 100 microvolts in amplitude and each less than 2 milliseconds in duration. These represent uncoordinated contractions of heart muscle (myocardium) fibers. This is a degrading and dangerous state and does require electrical intervention plus oxygen and cardiac medications in an effort to stabilize or regain a normal heart beat. Perhaps 40% of heart attack victims are in fibrillation when a paramedic arrives. Another 40% might be in bradycardia, tachycardia or asystolic status. The other 20% might have plugged heart blood vessels, bleeding, or other conditions that are not related to the electrical function of the heart muscle.

The present invention provides devices and methods whereby substantially lower voltages and currents may be used to successfully treat heart muscle arrhythmias.

All individual organs of the body are electrochemical in nature and operate on something approximating one volt to conduct their respective duties. Certainly the action of the myocardium (muscular contractile body of the heart) which contracts about one billion times in a life span, also conducts its business of pumping blood utilizing only about one volt of electricity at any point in time. Each beat is a cascading flow of myocardial contractile motions that squeeze blood from the four chambers of the heart and then accept a refilling of blood for the next cycle.

The heart is a pump with a closed system of arteries and veins with a natural duty to circulate oxygenated blood over the entire network of blood vessels. Oxygenated blood is red when it is rich with oxygen loaded into its red cells, called erythrocytes. Blood turns blue as carbon dioxide (CO2) and other waste products are loaded into its red cells, not now called "blue cells". The returning blue blood is pumped to the lungs to release the CO2 and other gaseous waste products. The red cells immediately uptake oxygen and continue their journey via the heart and into the blood vessels, to cyclicly do it all over again.

State of the art application of electricity for medical therapy to stop the fibrillation or quivering that is often encountered when a paramedic arrives on the scene of a heart attack victim, uses from 1,800 to 5,600 volts with 27 to 75 amps of current. The actual voltage and amperage that reaches the heart varies under Ohm's law by the resistance of the human or animal body and the integrity of electrode contacts to the body. Ohm's law states that voltage (V) equals the product of current (I) and resistance (R), or V=IR. Hydration of the skin under the electrodes also plays into the efficiency of the electrical therapy. There is approximately 50 to 150 ohms of resistance in the body depending on the hydration of live tissues. However, the most outer thin layer of dry skin can be 1000 ohms or higher. But high voltage can bust through that skin layer. Obviously the tissue is not as good a conductor as a metallic wire. However, because of the ionic nature of human or animal bodies it is possible to generate a specific waveform and cause it to enter the biological tissue and have an effect. Designers of external defibrillators anticipate a 50-ohm resistance load, but they know it could be somewhat higher.

Despite public perception, most of the people collapsing with heart failure, are not reached in time by paramedics to save them. Those that live because they received early defibrillation are often impaired from the cardiopulmonary resuscitation (CPR) process or by the high-voltage energy applied to their chest. The use of voltages that re in the range of 1,800 to 5,600 volts applied to the closed-bare chest of a human is a risky event. It is also risky to the medical personnel who must stop all contact with the patient or potentially be an electrocution victim themselves. The patient must sustain the large shock which conducts all over the body, with risk of burning out peripheral nerves and injuring any organ or system. There is a question of why such large voltage electric shock therapeutically even makes a positive outcome in the small minority of heart attack victims it saves.

The human body runs on small voltage within all of its systems including the brain and the heart yet all electric shock therapy consists of explosive bursts that are a risk to patient and treatment personnel. "Stand-Clear" is used by medical personnel to mean keep away or risk dangerous electrocution.

The usual action of the heart electrically begins by the sinoatrial node (SA node) firing a signal that then travels through known conductive pathways while activating contraction events as it goes. The SA node is actually a strip of electrochemical cells located on the radius between the vena cava and the right atrial chamber. Explained in simplicity, the conducted bioelectrical pulse activates in turn the atrioventricular node (AV node) and then respectively to various branches of the cardiac conductive pathways to complete a cardiac cycle from the top atrial chambers of the heart onward to the powerful ventricular chambers. The SA note repeats itself for the next round of activation of the electrical circuits which activate the pumping action of the heart all over again. The heart's duty is to circulate blood via the contractile ability of its various chambers, of which there are four, to repetitively contract and relax. Contraction pumps blood and relaxation allows the four chambers of the heart to refill with blood. The SA node electrical action is the beginning of the entire electrical activation system which causes the contractile cells which populate the myocardial muscle structure to react to this stimulation in an uncoordinated unison. The action of the contraction occurs more or less in harmony but this does not mean every cell contracts at the same time.

When observing the heart in an open chested subject, be it animal or human, this contraction appears as wave-like motions caused by the unsynchronized actions of myocardial muscle strands shrinking and stretching. The lack of synchrony is only mildly apparent. As the heart contracts cellular events are occurring so fast that the activation of the pumping action occurs with enough cells arriving at maximum shrinkage, contraction, within millionths of a second of each other. The fact that some of the contractile cells are a little late only adds to the final "push" of the blood out of the respective chamber.

The heart is alive so it can be expected that it will not have positive pumping actions that in any way approximate a man-made mechanical pump. The heart has cellular respiration and is nourished by the blood stream. The contractile cells of the myocardial muscle facilitates its operations by controlling the electrochemical environment of the actual contractile cell. This happens within the contractile cell by the changes in the electrochemical status as is required for polarization (contraction) and repolarization (replenishment and rest) to make changes in the electro-chemical status by moving ions in and out of contractile chambers via "wet" channels that have "gates" or "doors." This proper contraction of ions within the cell provides electrochemical energy to cause the contraction to happen. The signals from the SA and AV nodes add additional electricity to the electrochemical contractile cells to activate the contractile response. All of this electrical activity is measured in millivolts with the entire process never exceeding about one volt to cause the heart to pump blood.

When a heart contracts it is called depolarization and when it prepares itself to contract again it is called repolarization. Heretofore, it has been presumed that myocardium, or heart muscle, must be in a resting state lasting about 200 milliseconds before the depolarization can occur once again. This has been believed to be necessary because ions of the contractile cell need to replenish and rearrange themselves before the correct electrochemical balance is reached within the contractile cell. However, the heart is not limited to the conventional ideas of how contraction occurs and it does not necessarily need to rest before it can contract again.

In 1887 it was demonstrated that natural electrical impulses could be measured from the surface of the body in dog, man and cat. In 1903 the accurate electrocardiograph and the various deflections of the electrocardiogram used today identified respectively as p,q,r,s and t, were invented by William Einthoven. Thereafter followed a flurry of activity by mathematicians and scientists to study Einthoven's tracings of heart electrical deflections measurements as a way of explaining how the heart actually worked. In so doing they developed the idea that a heart made a contraction, either pumping or depolarization, followed by a relaxation, resting or repolarization, period. Out of this came the accepted theory that stated that no electrical impulse applied to the heart during the resting phase could make it reactivate and contract again. Cardiologists accepted that the heart had no capability to be contracted and held in that state for any length of time; certainly not for many seconds or even minutes. Consequently, no state of the art commercial electrical shocking device can hold a given waveform for many seconds or minutes. Present devices' defibrillation and pacing modes maximum output are unable to sustain a pulse for longer than about 80 milliseconds.

The natural contractile cell electrical activity ranges from approximately −100 millivolts (relaxation) to +20 millivolts (contraction) during a complete cycle. Among other things that can alter the exact voltage present in the contractile cell or cells are nutritional and medicinal. In addition emotional excitement, panic or sorrow can impact the performance of the contractile cells.

In approximately 250 milliseconds (ms) all of the events listed in Table 1 complete one cycle of the heart's electrical activity. The time depicted is for an activation by a bioelectrical impulse traveling throughout the heart's electrical conduction system for each event.

TABLE 1

| Event | Time for Activation (ms) |
|---|---|
| Atrial | |
| SA node sends impulse | 0 |
| Right atrium activated | 50 |
| Left atrium activated | 85 |
| P-Q interval delay | |
| AV node impulse arrival | 50 |
| Departure of impulse | 125 |
| Bundle of His activated | 130 |
| Bundle branch(s) activated | 145 |
| Purkinje fibers activated | 150 |
| Ventricular | |
| Right endocardium depolarized | 175 |
| Left endocardium depolarized | 190 |
| Right myocardium depolarized | 205 |
| Left myocardium depolarized | 225 |

The naturally-generated bio-electrical impulses required to conduct the business of the heart has been understood to consist of rather brief and simple activations at millivolt levels of excitation as shown in Table 1. Following that understanding, defibrillator designs fire electrical shocks at thousands of volts for ten to forty milliseconds duration. Such electrical therapy is almost universally delivered via a direct current coming from a dischargeable capacitor.

The need to conduct various kinds of surgical procedures on the surface of the heart or its blood vessels is complicated by the movement intrinsic to a living heart. Therefore, some surgical repairs are conducted by lowering the temperature of the heart until it can be stopped while a cardiopulmonary bypass machine, or heart-lung machine, keeps the patient alive by keeping blood circulation with oxygenation in tact.

Other procedures such as coronary artery angioplasty can be conducted on the moving and living heart. Also endoscopic pericardioscope has been employed to make surgical procedures less invasive and less expensive than open chest surgery. Such surgery when done open-chested by means of a standard midline sternotomy followed by entry into the pericardial sac is quite invasive and traumatic compared with the pericardioscopic procedures employed through several small incisions.

Cardiac ruptures are increasingly recognized by twelve lead electrocardiograms and have evolved into good predictors of impending rupture. With this diagnosis, impending rupture is prevented from proceeding to an actual fatal rupture. Endoscopic techniques are evolving that use fibrin glue or several other glues that can be used to effect a repair of small defects. Tissue adhesive and laser welding of myocardial injuries may require paralysis of the heart for a matter of seconds to a minute or two to allow precise location and procedure to effect a correction.

Tissue adhesives may eventually replace sutures which have frequently pulled through areas being operated on, especially if an infarcted area has been buttressed or oversewn. Myocardial tissues are in general very delicate and working surgically on them while they are in motion are fraught with difficulty.

Having an ability to stop the motion of the heart and then to allow a normal sinus rhythm return after the repair procedure is completed is a useful tool when coupled with the endoscope. With the advancing technologies in diagnosing ever smaller defects which are repairable with ever lesser invasive procedures, the ability to bring the heart to a stand-still electrically in the operating suite offers a new dimension to the cardiac surgeon.

The complexities of the human electrical system are not fully understood, as yet. Certainly the theories that date back to the early twentieth century of how the cardiac contractile cell is activated may be flawed since there was no capability at that time in history to test or evaluate those ideas. In these early theories the depolarization or contracting of the individual cardiac cell by an electric current was thought to occur rapidly and then the cell was required to undergo a refractory (resting period) before ionic changes could occur to prepare the cell to contract again (repolarization). These theories say that during the refractory period no stimulus of electricity, whatever its magnitude, could make the contractile cell activate.

In other words, the present theory suggests that a heart can contract but then must rest before it can contract again. Further, the theory says that the ions that were driven out of the cell are recovered very much more slowly than they were driven out before a new contraction can be done. This is a sort of ionic replenishment and depletion.

It appears that certain electrical waveforms can direct the contractile capacity more firmly and that such waveforms do not require long refractory (rest) period before a new contraction can happen. It has been demonstrated in the animal heart, that a heart can be held in a contracted state for many seconds without giving it a rest (refractory) period. Furthermore, it appears that long-cycle contractile period extinguishes fibrillation and allow for rescue by making the myocardium susceptible to the reestablishment of a cyclic beat. But pulsing must start within a certain number of milliseconds after the release of the long contraction in order to recover heart function more surely and do this with low voltage.

The waveforms of the present invention can play a role in conditioning the ionic population of the contractile cell so that recovery from fibrillation can result in resuming pulse pacing after the extinguishment of fibrillation wave fronts.

There is a significant problem in clinical practice wherein hearts often return to fibrillation after defibrillation instead of recovering by beating (usually slowly). Current treatment practice is to await cardiac reaction by waiting and watching after a defibrillation shock. If a beat begins, usually slow in rate, medicinal injections are used to speed it up so that good oxygenation and blood circulation can be recovered by the victim.

A waveform is the specific mathematical shape of an electrical energy burst that is generated by an electronic device and sent, like a bolt of lightening, in the case of a defibrillator, into the human body. An electrical waveform is generated as a definable pulse of electricity which is either a transient burst of energy into a storage battery. The result is after enough electrical potential is replaced in the battery it is able to turn-over the starter which in turn allows the engine to run and in turn recharge the battery. An automobile utilizes another twelve volt source and several minutes or longer to jump-start a dead battery. This is not so with the heart, where thousands of volts in millionths of a second is the usual therapy for heart attack victims.

The shape of a waveform is its graphical representation. This shape can vary in many ways, such as positive or negative or longer or shorter. In addition, the ascending-slope of electricity can have infinite variations as can the descending-slope prior to extinguishment of the electrical burst of energy. Energy can be pulsed with spaces between the actual electrical stimulus -- and do this so fast that no detection of such "energy blanks" can be seen except on an oscilloscope. Usually a capacitor is used to store the electrical energy before it has released it all at once to provide the shock to the chest.

Present-day waveforms utilized in defibrillators are truncated, exponential, damped sinusoidal and trapezoidal. Biphasic variants are available which reverses the polarity in the middle of the brief but high-voltage shock. The duration of a waveform generated from a present-day closed-chest defibrillator is usually about 20 but not likely longer than 40 milliseconds; for an external cardiac pacer it is typically 20 to 40 milliseconds.

Such waveforms utilized by state-of-the-art products have changed little from their earliest design. Existing external defibrillator technology has developed a marketplace and is producing product to service its customers, with little change in output waveform. However, implantable cardiac products are taking more advantage of software and chip technology to better control the outputs of their products but they still use 310 to 750 volts for defibrillation.

An objective of the present invention is to apply lesser voltage, but in a special waveform which exerts more delicate control of the contractile business of the heart. The present invention uses a different electronic waveform and significantly lower voltage for conducting defibrillation and pacing, as well as for cardiac paralysis to allow surgical treatment. This lower voltage is actually closer to the electrical energy generated biochemically by the human or animal heart than is currently being used for defibrillation. This technology uses voltages closer to the kind of voltage that can "key" into the ionic control of contraction. Consequently, much lower voltage and amperage can be used to treat heart attacks. This lower voltage approach is also useful in implantable devices designed for either defibrillation or pacing. The long-term availability of lower voltage and special waveforms is gentler on the cardiac structures.

The present invention provides an ability of up to three minutes of electrical paralysis at relatively low voltage. Such electrical activity can be ordered up in combinations of seconds and minutes. The device can contract the myocardium and hold it in a contracted predetermined period and then release it so that circulation and cardiac tone can be reestablished. At will the surgeon can also re-paralyze the heart to continue the medical procedure or repair.

The present invention embodies defibrillation ability as well as a means to deal with asystole, tachycardia or bradycardia. The ability to select the kind of waveform shape as well as voltage output via an amplitudinal selection section provides capabilities not available within the state of the art defibrillation and pacing equipment.

SUMMARY OF THE INVENTION (DISCLOSURE OF THE INVENTION)

The present invention is of a monolithic device for providing defibrillation and pacing of a heart comprising: defibrillating circuitry and pacing circuitry which engages once defibrillation has been accomplished. The invention is also of a device for providing defibrillation of a human heart from outside the body comprising defibrillation circuitry having an electromotive force of less than or equal to approximately 200 volts. The invention is further of a device for providing pacing of a human heart from outside the body comprising pacing circuitry having an electromotive force of less than or equal to approximately 200 volts. The invention is additionally of a device for providing defibrillation of a heart comprising digital circuitry for generating a direct current waveform to the heart. The invention is yet further of a device for providing pacing of a heart comprising digital circuitry for generating a direct current waveform to the heart.

The invention is also of a method for providing defibrillation and pacing of a heart comprising: defibrillating the heart; and pacing the heart within approximately 20 msec of cessation of step a). The invention is further of a method for providing defibrillation of a human heart from outside the body comprising defibrillating with an electromotive force of less than or equal to approximately 200 volts. The invention is additionally of a method for providing pacing of a human heart from outside the body comprising pacing with an electromotive force of less than or equal to approximately 200 volts. The invention is still further of a method for providing defibrillation of a heart comprising digitally generating a direct current waveform to the heart. The invention is yet further of a method for providing pacing of a heart comprising digitally generating a direct current waveform to the heart.

The present invention is also a device for generating waveforms for myocardial control and the device comprises means for providing variable low voltage waveforms wherein each waveform has at least one pulse. The device further comprises means for varying the voltage magnitude of each of the pulses of the waveforms to selected voltages. The device further has means for varying the polarity of each of the pulses of the low voltage waveforms to selected polarities. Means for providing a refractory period between selected ones of the pulses of the waveforms are also included in the device. The device can further comprise means for varying the pulse width of each of the pulses of the waveforms to selected widths.

The present invention is further a method of controlling the myocardium and comprises the steps of generating variable low voltage waveforms that each comprise at least one pulse, and applying a selected waveform to the myocardium for a selected period of time. Generating variable low voltage waveforms, each having at least one pulse, comprises varying the voltage magnitude of the pulses to selected magnitudes. The step of generating variable low voltage waveforms further comprises varying the polarity of each of the pulses to selected polarities, and can also comprise providing a refractory period between selected ones of the pulses of the waveforms. Generating variable low voltage waveforms can also comprise varying the pulse width of each of the pulses to selected widths.

A primary object of the present invention is to provide means by which substantially lower voltages and currents can be used to control cardiac arrhythmias.

A primary object of the present invention is to provide an apparatus having selectable voltages and a family of waveform shapes to treat the heart.

Another primary object of the present invention is to utilize significantly weaker electrical forces to provide myocardial control and cardiac paralysis.

A primary advantage of the present invention is that the voltage effects on the patient are reduced.

A primary advantage of the present invention is that it is lightweight yet can operate for durations of three hours or more.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 3 follows FIG. 2, but with a body resistance of 100 ohms;

FIG. 4 follows FIG. 2, but with a body resistance of 200 ohms;

FIG. 5 follows FIG. 2, but with a C-FIB energy of 144 joules;

FIG. 6 is a schematic of the preferred hardware of the invention;

FIG. 7 is a diagram of the preferred switch settings of the hardware of FIG. 6;

FIGS. 8(a)–(c) is an electrical schematic of the preferred waveform generation circuitry of the invention;

FIG. 9 describes the pins shown in FIGS. 8(a)–(c);

FIGS. 10(a)–(b) is a schematic of the board components corresponding to FIG. 6;

FIG. 18 is an example waveform to be used for myocardial control in accordance with the present invention.

DESCRIPTION OF THE PREFERRED EMBODIMENTS (BEST MODES FOR CARRYING OUT THE INVENTION)

The present invention is of a system to control human and animal hearts to treat arrhythmias. The invention is intended to override an impaired human or animal heart electrical system and to provide a life-sustaining heart beat. In an external embodiment, the invention superimposes and conducts electrical current via stick-on, non-invasive electrode pads to stop damaging or inefficient heart contractions or fibrillation. In addition electrical energy is applied to the heart in a manner that captures its control and serves as the regulatory force to compel the heart to contract in a manner that circulates blood throughout the body. The purpose of the system is to cause all four chamber of the heart to contract forcefully so as to pump blood and immediately relax so as to allow all four cardiac chambers to fill with blood. The capture of the heart is aimed and causing a pumping and refilling of blood at a rate that causes oxygenation of humans or animals tissues and organs in a manner consistent with life. While the device contracts all four chambers of the heart simultaneously, the normal heartbeat contracts the upper (atrial) chambers first and then the lower (ventricle) chambers last.

Figure 1:
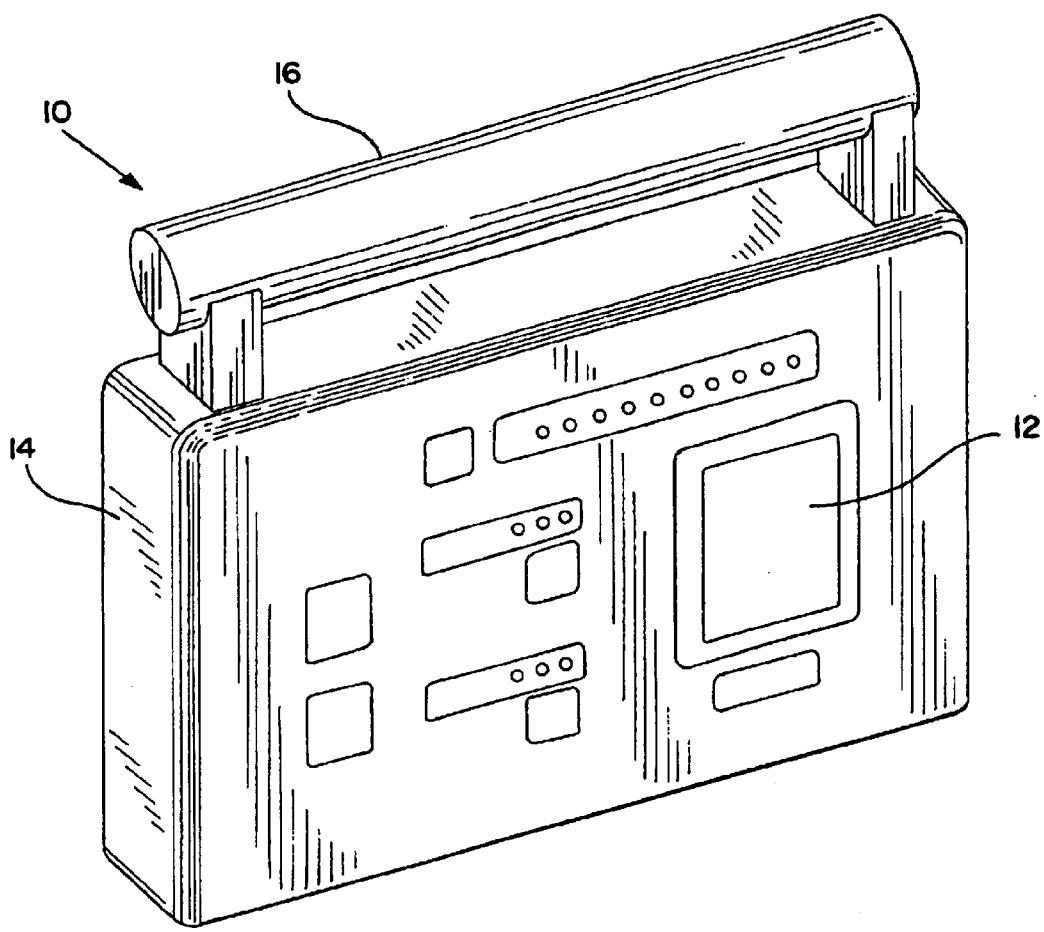
FIG. 1 is a perspective view of the preferred control unit of the invention.
Figure 2:
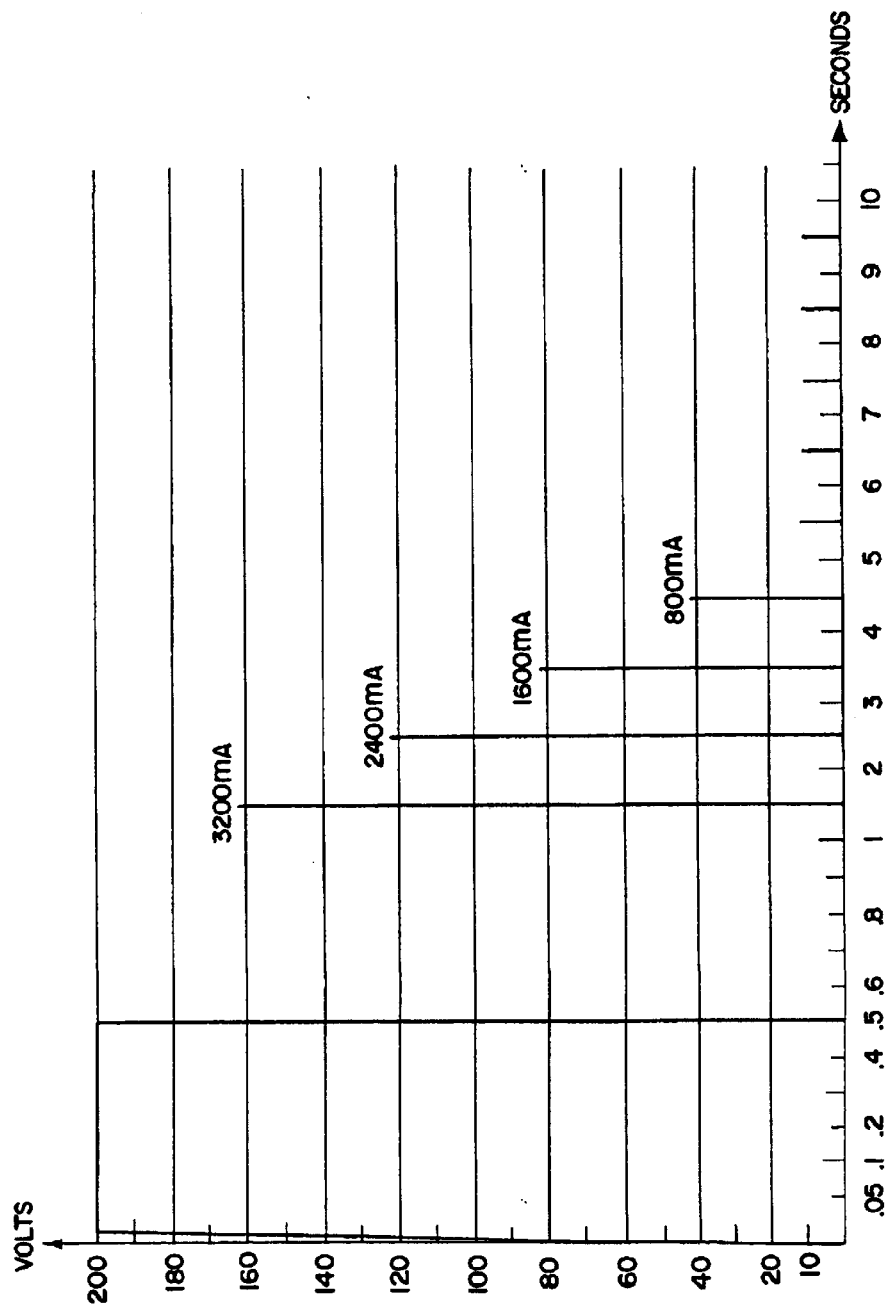
FIG. 2 is a graph of the counter-fibrillation (C-FIB) waveform of the invention followed by immediate external pacing, with body resistance of 50 ohms, C-FIB energy of 400 joules, pacing rate and pulse width of 60 bpm and 20 msec, and pacing current of 200 mA 5 seconds after C-FIB.
Figure 8C:
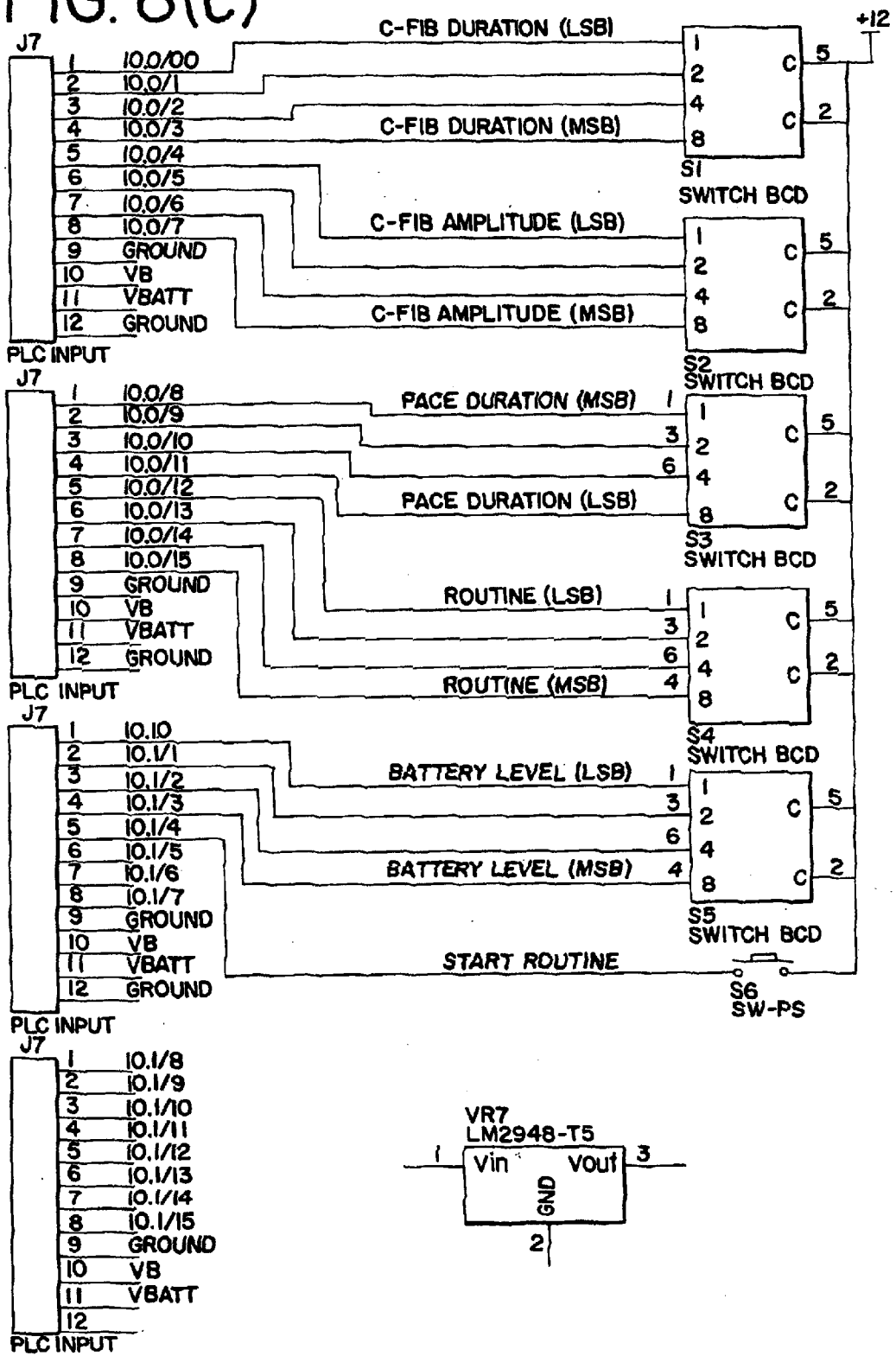
Figures 1, 10:
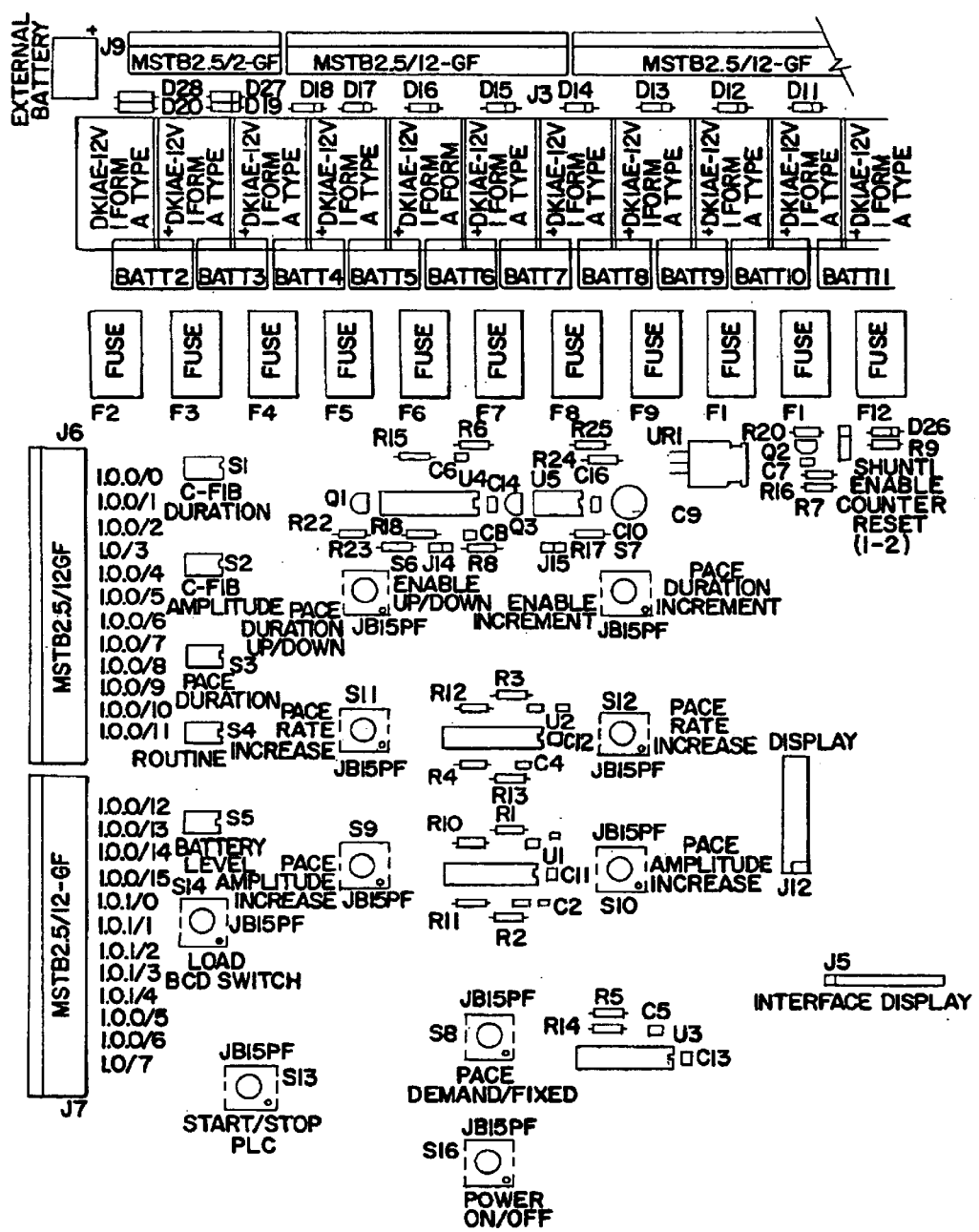
Figures 2, 10:
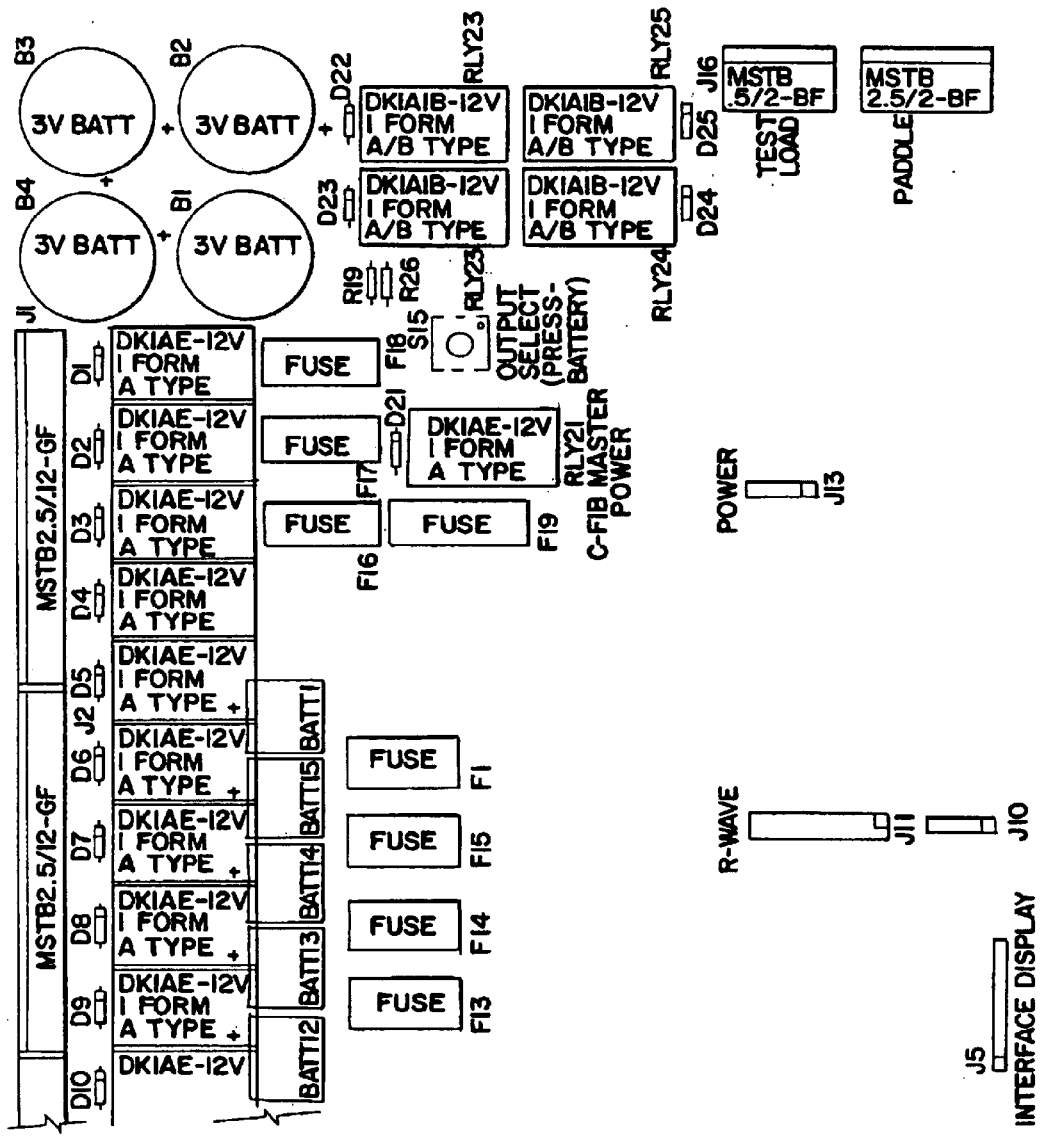
Figure 11:
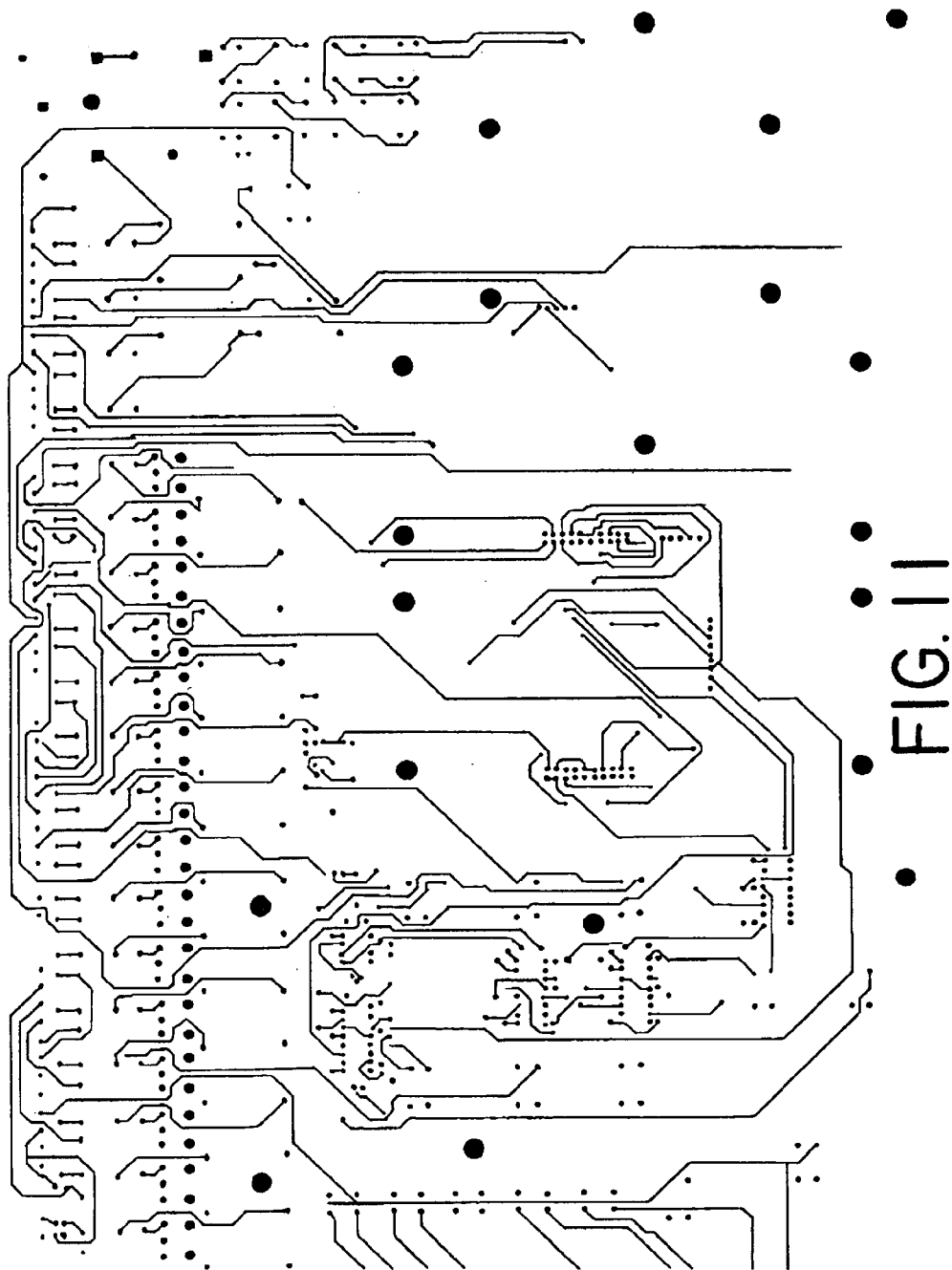
FIGS. 11(a)–(b) is a trace diagram of the solder side of the board corresponding to FIG. 6.
Figures 12A, 12B:
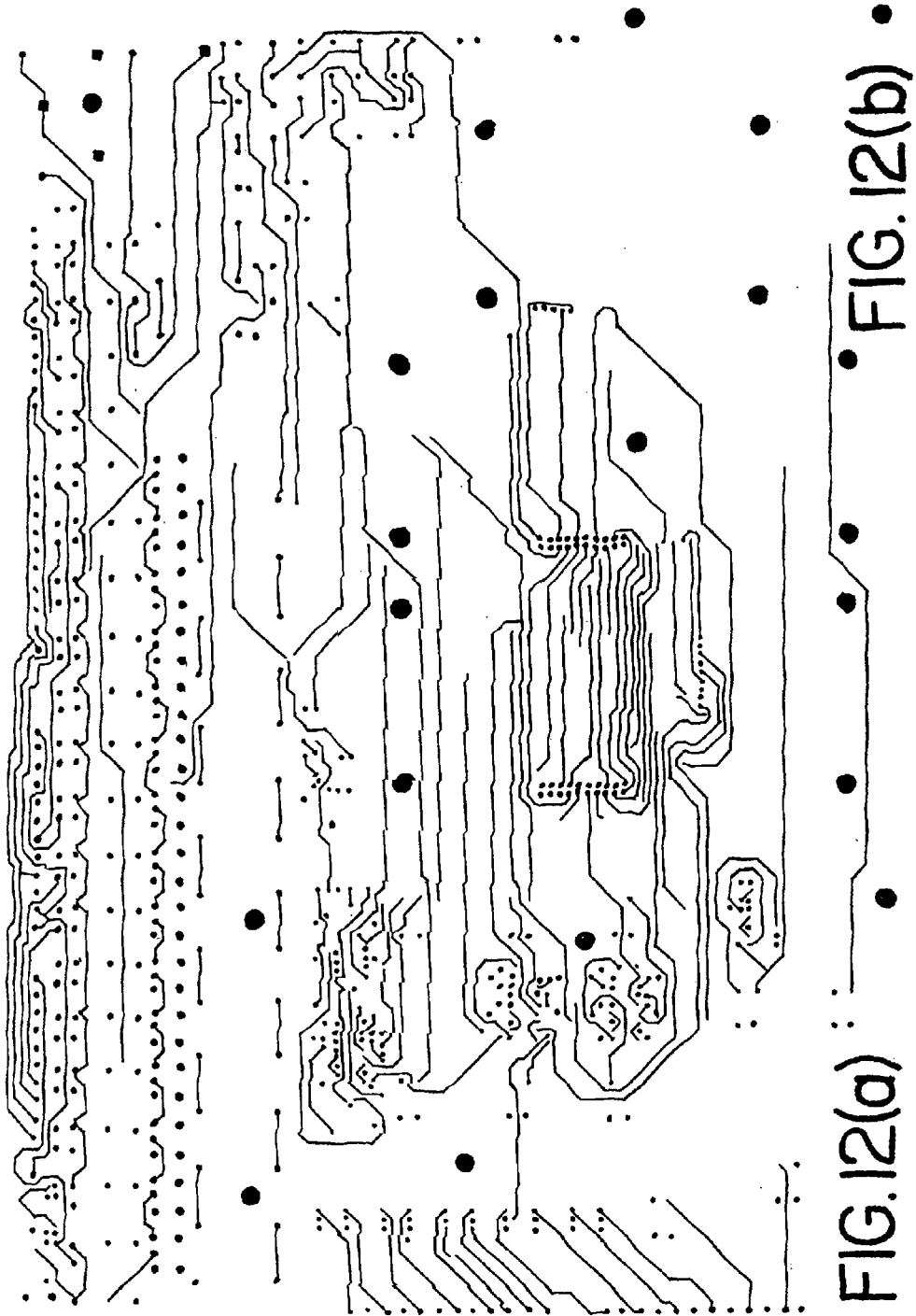
FIGS. 12(a)–(b) is a trace diagram of the component side of the board corresponding to FIG. 6.
Figures 13A, 13B:
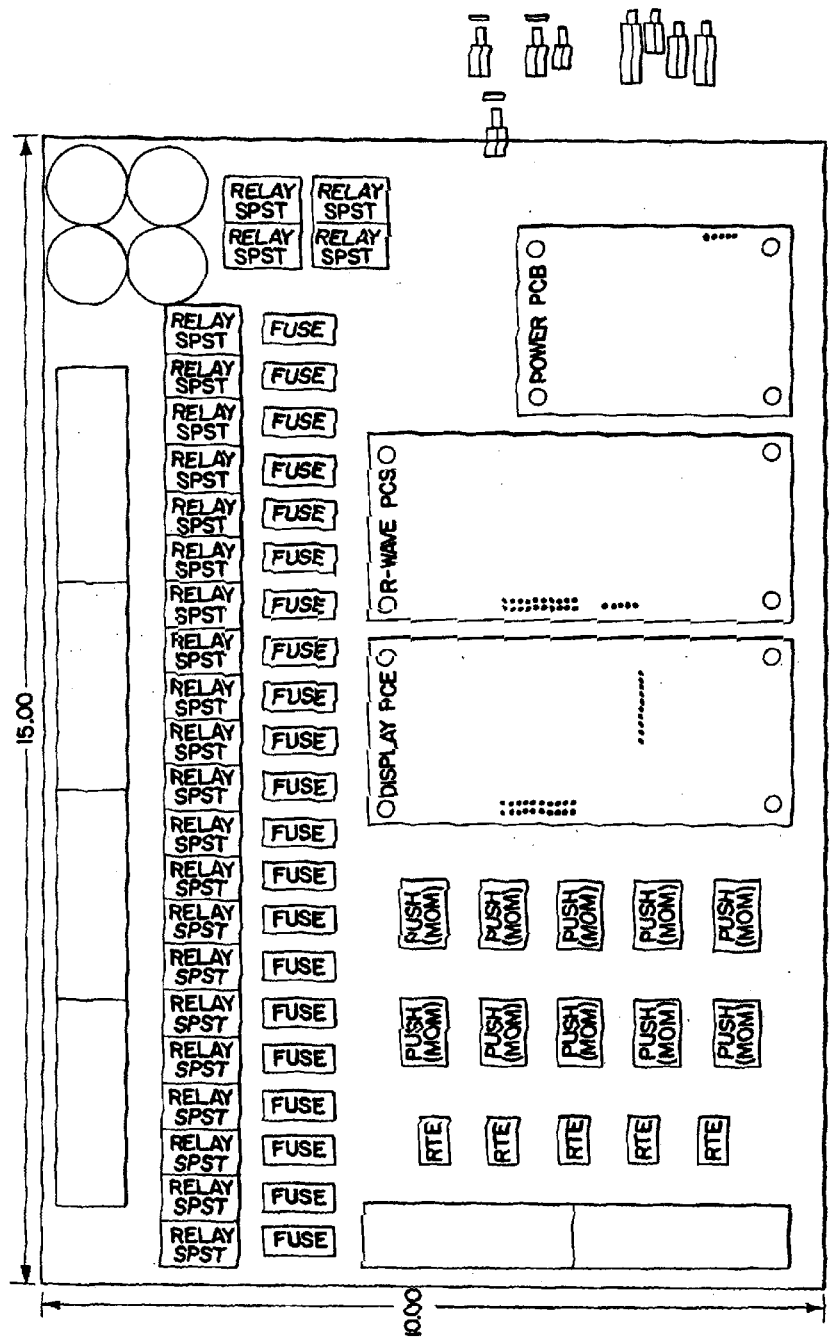
FIGS. 13(a)–(b) is a schematic of the board component slots corresponding to FIG. 6.

Referring to FIG. 1, the device 10 of the present invention provides for the electrical control of the heart muscle and preferably presents electronically monitored feedback on a small screen 12 to provide understandable data for medical personnel. The screen allows presentation of the sinus wave shape, heart rate and records and stores this information for medical record usage. Preferably, voice messages prompt the paramedic after the pacing and sensing electrodes have been applied to the patient, including: (1) no detectable beat—check connections; (2) fibrillation or erratic beat; (3) bradycardia; (4) tachycardia; and (5) stable heartbeat. The main use of the external embodiment of the invention is for first-responder treatment of acute cardiac emergencies, being non-invasive in that it does not pierce the skin.

Every aspect of output is employed in device 10 which preferably weighs approximately 3 to 4 pounds and is preferably battery operated. Device 10 accommodates all types of electrodes such as stick-on, sew-on, hooked-in or those emplaced by transvenous wire. In addition, hand-held paddles can be used directly on the myocardium for certain procedures. The panel layout of device 10 can of course vary. Batteries are preferably rechargeable lead-acid gel types. Device 10 is self-testing as to viability of its output circuits and battery status.

The use of the present invention for the resuscitation of animals ranging in size from small dogs up to large zoo-kept mammalian species is possible with lower or higher power units for correspondingly smaller or larger hearts than humans have. The heart resuscitation animal models indicate that the larger the animal the larger the heart and the more power will be required to control that heart. The human electronic device is appropriate to treat both adults and children. To accomplish this, the device preferably features an operator controlled amplitude range of sufficient expanse to cover anticipated patient size and hydration status.

The invention is preferably sealed to be usable in wet environments and may be cleaned and disinfected with selected chemical disinfectants. The external embodiment is powered by, for example, one or more rechargeable 12-volt lead-acid gel batteries within the main section 14. In addition, a cylindrical handle 16 located on the left side of the unit houses alkaline D-cells. The D-Cells can be changed while pacing or counter-fibrillation continues via the internal 12-volt battery(ies).

The invention preferably combines counter-fibrillation with assessment and control functions. Counter-fibrillation utilizes relatively low (preferably less than approximately 200 volts) electrical energy which calms or contracts the heart for ½ to 5 seconds and then runs a pacing program (preferably five to 60 seconds, and most preferably 25 seconds) followed by operator selection of subsequent pacing rates and modes. There are two pacing modes, demand or fixed.

In the external embodiment, up to a certain number (preferably four, three or up to six being acceptable) of sensing pads (approximately 1.5 inches diameter) are placed on the chest and/or back or on pulse points found at the wrists or elsewhere on the body to detect rate of heart function. The sensing pads lead to electronics that immediately report cardiac performance or lack of it. That information is flashed on a screen for operator interpretation. Such information includes basal heartbeat rate, if any, and determines if it is chaotic fibrillation, no-beat or too slow or fast. In addition, it is determined if the heart is fibrillating or is asystolic.

FIGS. 6–13 illustrate the preferred hardware of the invention, including a programmable logic controller, an external transcutaneous pacemaker, an interface circuit board, and a battery pack. The programmable logic controller preferably includes customizable software, 24 inputs, 32 outputs, two kilobytes of reprogrammable memory, and input/output expansion capabilities. The external transcutaneous pacemaker provides a constant current source up to 300 ohms, discrete amplitude range adjustment from 20–200 mA in 10 steps, discrete rate range adjustment from 40–220 bpm in 10 steps, fixed and demand mode pacing, adjustable pacing duration from 20–100 msec, and complete manual and software control.

The interface circuit card provides a counter-fibrillation voltage of 3–192 volts, programmable logic input definition switches, programmable logic outputs, and DC power utilization. Example inputs and outputs are shown in FIGS. 6–7. Input switches may include counter-fibrillation duration of 0.5–5 sec over 10 steps, pacer current amplitude starting point from 20–200 mA, counter-fibrillation amplitude setting least significant nibble, pacer rate starting point from 40–220 bpm, counter-fibrillation battery level most significant nibble with two upper bits set as "Don't Care" for use as a 2" multiplier which extends the maximum voltage from 48 to 192 volts, pacer pulse duration of 0–512 msec with 32 msec resolution, choice of routines, and start/stop control. Output switches may include 3–192 volts over 20 outputs, master output control, counter-fibrillation and pacing output control selector, biphasic control, pacer on/off, rate, current amplitude, demand/fixed pacing mode, and rate counter reset and pulse duration controls.

A number (preferably three) of pacing pads of 8 to 12 square inch electrode area each are placed, such as with two on the chest and one on the back. The impedance of the body is ascertained to select the starting energy levels for both the counter-fibrillation and pacing modes. These pads do multiple duty as they determine impedance and also are used to apply the counter-fibrillation current and/or the appropriate electrical pacing energy.

The system detects the heart status any time during the use of the device provided the sensing and counter-fibrillation/pacing pads are in place on the body of the patient. In some instances the small sensing pads provide information and in other cases counter-fibrillation or pacing must stop momentarily (1 to 5 seconds) for information on heart performance to be ascertained.

The counter-fibrillation system can apply monophasic, biphasic or triphasic direct current via the pacing pads so as to paralyze the heart muscle (myocardia), but a multiphasic counter-fibrillation waveform is preferred such as discussed in U.S. Provisional Patent Application Serial No. 60/079,514. The time required for stopping fibrillation of the heart shall preferably ranges from ½ second up to 5 seconds. Once the heart is counter-fibrillated, the sensors detect calmness or chaos characteristics of the heart and pacing is initiated at the same instant (preferably within 20 msec) that the counter-fibrillator releases its hold on the myocardia. Pacing is preferably operator controllable from 50 to 200 beats per minute. Initial pacing is automatically applied as part of the counter-fibrillation module. The first beats are at higher electrical amplitude to insure capture and control of the heart. Sensors inform the operator, along with observation of life signs, if capture is lost. The operator can repeat the pacing program or can raise the amplitude manually to attempt a re-capture and gain electrical control of the heart's biological electrical pacing system.

When pacing is occurring at the rhythm selected by the operator, the operator may elect to engage a demand mode and transport the victim to the hospital. The demand mode "listens" via the sensors and warns the operator by audible alarm and visually on the monitor screen if capture is lost. The operator may try to re-capture by manual control of pacing rate and amplitude or he can default to the pre-programmed pacing event if capture and control of the heart cannot be attained.

The invention, which is battery operated for up to approximately 3 hours, stabilizes a heart within approximately one minute after applying of the electrodes, provided the operator has arrived within about five minutes of a heart attack. The fully charged batteries shall be operative for a minimum of 3 hours, but this can be extended by changing the alkaline batteries. Batteries can be changed quickly with little or no interruption of pacing once the patient is stable. The cylindrical case contains alkaline batteries which can be changed as in a flashlight. The rechargeable internal lead-acid-gel 12-volt battery(ies) in the main body of the invention supplies electricity while the alkaline batteries are changed. The cylindrical battery case also serves as a carry-handle. The 12-volt main battery(ies) can also be changed quickly if required. The entire system, including both pacing and counter-defibrillation module, preferably weighs less than five pounds. In models without counter-defibrillation, the weight preferably is less than three pounds. Weight does not include electrodes, sensing pads, or the wiring harness.

The present invention is also of a method of gaining emergency electrical control of a fibrillating heart. The usual cardiac medications, oxygen administration and other treatment can be utilized simultaneously or after cardiac counter-fibrillation treatment is applied. The invention can be used alone for stopping fibrillation or it can be part of a system that deals with all heart arrhythmias. Rather than an analog signal, a digital, software driven, signal of constant direct current is employed to bring a fibrillating heart to a standstill very quickly. This is important because the longer the duration, the lower the voltage amplitude. The longer duration and lower voltage amplitude can result in the same amount of energy being applied as used today with defibrillators, but usually is much lower in energy. However, the invention begins at a lower electrical energy and then steps up as required until the heart fibrillation ceases. The nominal amount of time applied to each counter-fibrillation power level is about 1/2 to 5 seconds.

When the fibrillation has stopped, the counter-fibrillation electrical energy is released by the software which then instantly activates a special brief burst pacing program to establish a heart beat. The burst pacing program can last up to preferably 25 seconds. The energy for this particular heart pacing starts high and with each contraction of the heart steps the electrical energy downward by about 15%. If "capture" of the heart is lost, then sensors increase the next electrical energy pulse by an amount, preferably by 30%. If capture is not regained, the algorithm program returns electrical pulse to the highest pacing power and runs that program as long as capture is maintained while reducing pulse power by 8 to 10% every two or three pulses until it maintains control of the heartbeat at a fixed rate wherein the information aspect of the unit prompts the paramedic to select a fixed rate pacing and adjust the power as he deems appropriate while transporting the patient to a hospital. Capture is determined by sensors that detect either electrical activity via electrode pads, mechanical activity through blood pressure and blood flow detection, or both. The sensors, which may be standard, off-the-shelf items, are fed back to the logic control circuitry that makes decisions based upon the sensor's output.

The paramedic can further tailor the pacing program treatment aspect by continuing fixed-rate pacing or switch over to demand mode which monitors the heart and only paces if the victims heart beat drops below a selected rate. The paramedic may also select a waveform or waveform variation stored in software of the control system. Thus, if a patient's heart is beating on its own the unit merely stands by to catch any decaying beat rate. Enough beats are inserted during a minute period to equal the amount called for by the paramedic. Rate selection for demand-mode is operable only between 50 and 120 beats per minute. While fixed-rate pacing can be utilized to pace a heart throughout a range of 50 to 200 beats per minute.

The formula for energy utilized for counter-fibrillation is given by J=Voltage$^2$×seconds/Resistance. If the analog signal is transformed into a constant DC signal of greater duration, then a substantial reduction in voltage can be achieved. For example, assume a patient's body resistance is 50 ohms and in order to reset the heart it'll require 360 joules. With the present day analog signal technique, it would take approximately 650–1420 volts. Now assume that the new constant DC signal duration is stretched out to 0.5 seconds. The voltage required to do the same amount of work is now 190 volts. The total voltage can be less than 200 volts but more than 60 volts for adults. Children in fibrillation can be expected to be treated with 40 to 120 volts. The selection of voltage will be relative to the hydration of the patient and their relative body size and frailty. Obviously, a much safer situation for doctors, nurses, emergency personnel and the patient. Implantable device voltages are approximately four to eight times less than voltages needed with non-invasive stick-on electrode pads of the invention.

The counter-fibrillation signal can be described by a sharp rise in voltage (slope) for approximately 3 to 5 milliseconds, where it will reach the full DC value and then be maintained (held at constant value) for a variable long duration followed by a decay in voltage very similar to the slope of the rise. The method for up slope or down slope may be in small digital steps or angular cascade in many electrical patterns. This electrical signal can also be reversible as to polarity by the operator. The counter-fibrillation force on the heart can be applied from ½ second up to 5 seconds. Time and voltage are gradually increased via instructions from the installed program.

The counter-fibrillation system of the invention and its electrical and electronic controls can be combined with or inserted or added into other emergency cardiac systems as a drop in module. Additionally, the system can be designed into more complex cardiac care systems. It can also be utilized as a stand-alone compact system for first responders to cardiac emergencies.

The electrical patterns preferred for the applications discussed above are shown in FIGS. 2–5. These electrical patterns indicate some of the approaches to stop fibrillation in a human or animal heart. Some variations of these patterns may be made but the inventors are certain that those presented herewith shall stop fibrillation in both human and animal hearts at much lower power than traditionally used. This invention shall more surely stop fibrillation and directly cause heart pacing to occur and do this faster than is currently possible with pre hospital cardiac victims.

The present invention may be used to stimulate contractions of other muscles than the heart where desirable.

The present invention also includes a family of low-voltage waveforms, all adjustable in time, direction of polarity, and electrical intensity. The waveforms are for extinguishing aberrant rhythms including quivering without a definable beat, known as fibrillation. In addition, these waveforms are direct current and have variable voltages from 1 to 500 volts. These waveforms are delivered from the device and are for therapeutically treating human or animal hearts either externally in closed-chested subjects or internally with implantable electrodes via transvenous entry or open-chested for insertion. The waveforms can also be generated from externally applied electrodes such as the hand-held or stick-on types. The direct current waveforms are completely variable in every way with regard to intensity, polarity, frequency and duration. Variations of these waveforms are limited only by the capability of the controlling software. Additionally, the waveforms can be varied in unlimited ways within the designs presented in the figures. The purpose of these waveforms is to control the heart with vastly weaker electrical forces than are presently utilized within the state-of-the-art.

Voltage levels for any waveform, pulsing, or myocardial paralysis preferably ranges from 3 volts up to 86 volts for open chested humans or animals of less than 200 pounds in presurgical body weight. Current flow capability preferably does not exceed 5 amps, assuming heart impedance of from approximately 75 to 150 ohms.

Figure 15:
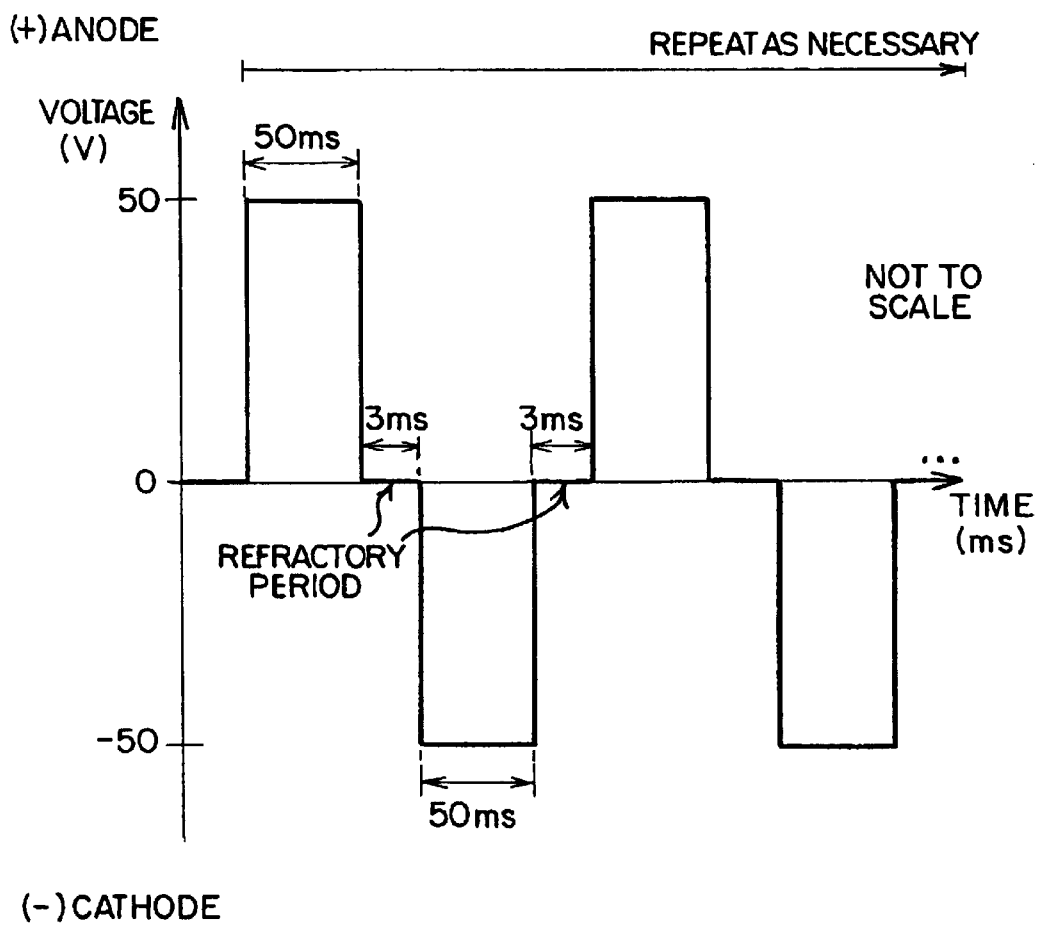
FIG. 15 is an example waveform to be used for myocardial control in accordance with the present invention.

FIGS. 15–18 provide further examples of the variable electronic waveforms that can be generated by the device which are capable of controlling the heart. Generally, each pulsed waveform changes polarity five times within approximately 250 milliseconds, and the refractory period is preferably between one and five milliseconds. FIG. 15 shows a direct current waveform alternating in polarity between +50 and −50 volts. A refractory period of 3 milliseconds is shown between each voltage pulse applied to the heart. Pulse widths are shown to be 50 milliseconds. Although this particular configuration is demonstrated, pulse widths, refractory periods, and voltage magnitudes are variable within the basic configuration of this figure. Oscillations can be included in the refractory periods and can also ride upon the pulses.

Figure 16:
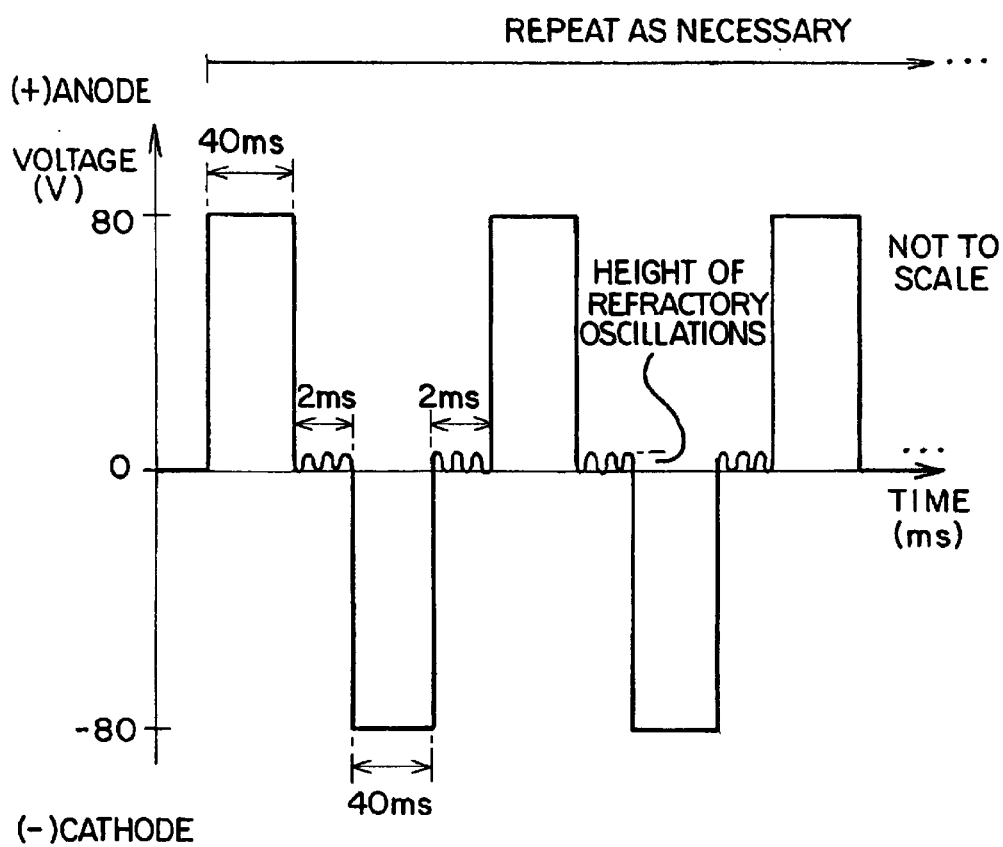
FIG. 16 is an example waveform to be used for myocardial control in accordance with the present invention.

FIG. 16 represents another direct current waveform which alternates in polarity between +80 and −80 volts. The refractory period is comprised of oscillations. The pulse widths are 40 milliseconds. Approximately three oscillations occur during each refractory period of two milliseconds. Magnitude and polarity of refractory oscillations can vary as well as the magnitude of the positive and negative voltage.

Figure 17:
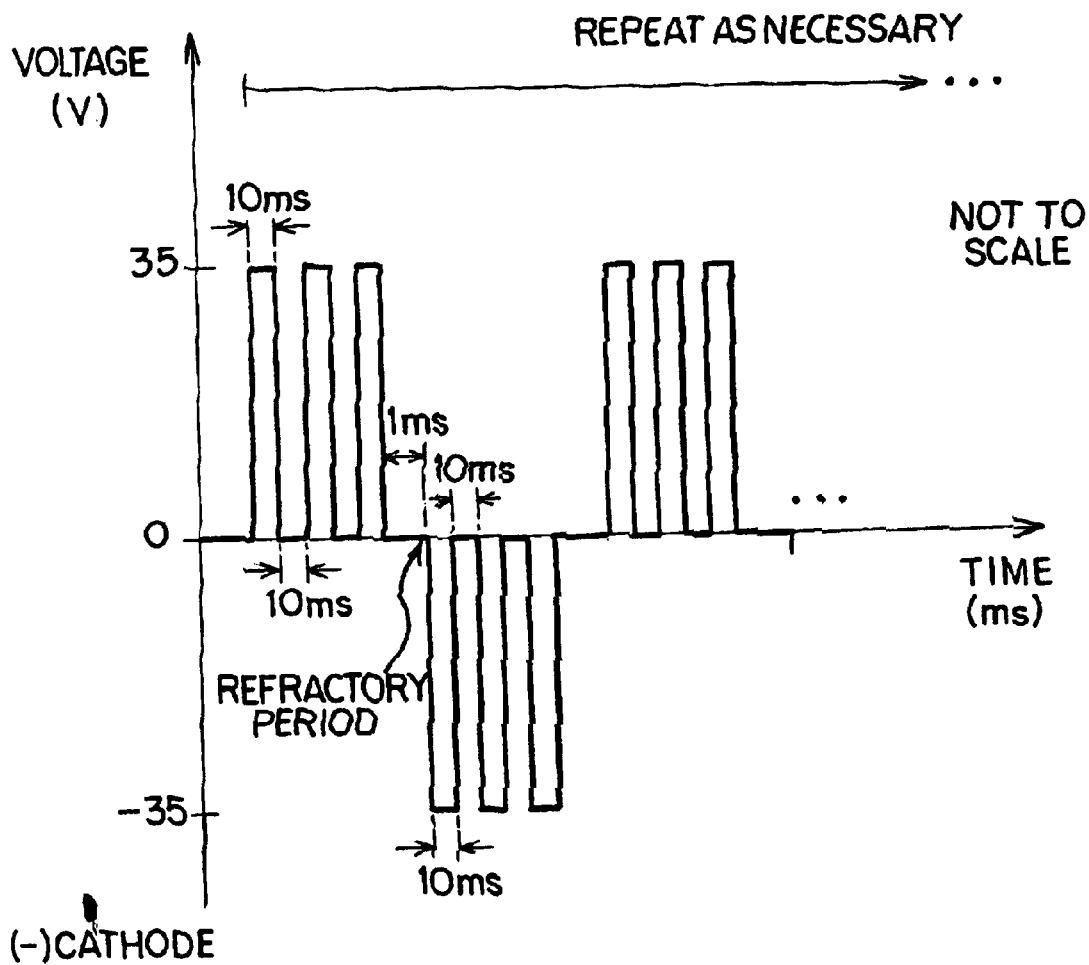
FIG. 17 is an example waveform to be used for myocardial control in accordance with the present invention.

FIGS. 17 and 18 also represent direct current waveforms alternating in polarity. Pulse widths, refractory periods, and voltage magnitudes can all vary. All figures show periodic waveforms although they need not necessarily be periodic.

In each of the electrical waveforms the time that the waveform is applied to the heart varies with respect to the function intended. For example, the waveform of FIG. 16 could be applied to the heart continuously for approximately 750 milliseconds in order to stop fibrillation and to paralyze the heart. The waveform of FIG. 16 can be applied continuously for approximately 5 seconds to paralyze the heart.

Therefore, voltage, magnitude and polarity, refractory period, refractory oscillation frequency and magnitude, and pulse widths can all be varied to provide control of the heart muscle. Furthermore, the waveform can be applied to the heart for longer time periods up to five seconds, or perhaps as long as three minutes in order to paralyze the heart. Approximately 750 milliseconds application upon the heart of any of the waveforms exemplified in FIGS. 15–18 will provide defibrillation. Longer periods, beyond approximately one second or more will paralyze the heart.

With the electrical waveforms shown in FIGS. 14–18, it is possible to hold a myocardium in a contracted state for at the very least five seconds and potentially for thirty seconds or even for several minutes. Also fibrillation and other aberrant cardiac rhythm disturbances can be extinguished during the process of holding the myocardium in a contracted state. Further, after the heart is held in a contracted state and the various aberrant wave forms extinguished, reprogramming via the software directs the selected waveform to act in a repetitively pulsing manner to contract and release the contractile capacity of the heart to allow pumping and refilling of the respective chambers to make ready for another pumping cycle—on infinitum. Clinical decisions on the use of the waveforms are made by the emergency medical staff while the patient is transported to the hospital. While in the hospital emergency room, operating room, or recovery room, the various waveforms selected can be adjusted as required by physicians with the device's software.

Industrial Applicability

The invention is further illustrated by the following non-limiting example.

Example

Figure 14:
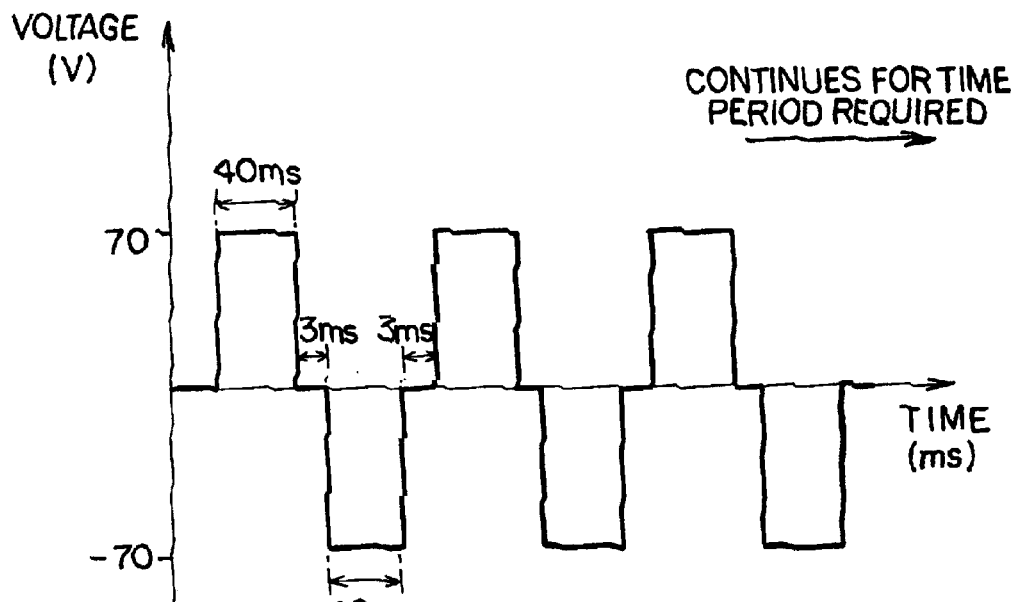
FIG. 14 is an example waveform for performing cardiac paralysis in accordance with the present invention.

For example, the user may choose the waveform in FIG. 14 after testing the patient's impedance and choosing the appropriate settings on the device to provide cardiac paralysis during surgical treatment. First, waveform shape selection is chosen for the desired shape. Second, the duration of cardiac freeze is set to 5 seconds. Waveform designate is adjusted in height, width, and refractory time to program the specific parameter of the waveform desired. Height is adjusted to 70 volts, width is adjusted to 40 milliseconds, and refractory time is adjusted to 3 milliseconds. With these settings, the waveform of FIG. 14 is continually applied for 5 seconds producing 5 seconds of paralysis of the heart muscle.

The preceding examples can be repeated with similar success by substituting the generically or specifically described operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A monolithic device for non-invasively providing defibrillation and pacing of a heart, said device comprising:
    low voltage means for defibrillating the heart; and
    means for pacing the heart once defibrillation has been accomplished.

2. A device for non-invasively providing defibrillation of a human heart from outside of a human body containing the heart, said device comprising:
    means for generating an electromotive force of less than or equal to aproximately 200 volts; and
    means for applying said electromotive force to defibrillate said heart.

3. A device for non-invasively providing pacing of a human heart from outside of a human body containing the heart, said device comprising:
    pacing means having an adjustable current amplitude range of between approximately 20 milliamps and approximately 200 milliamps; and
    means for applying said current to said heart.

4. A non-invasive device for modulating myocardial functioning, said device comprising:
    means for generating variable low waveforms similar to waveforms naturally produced by a body each comprising at least one pulse; and
    means for applying said waveforms to defibrillate said heart.

5. The device of claim 4 further comprising means for varying the voltage magnitude of each of said at least one pulse to selected voltages.

6. The device of claim 4 further comprising means for varying the polarity of each of said at least one pulse to selected polarities.

7. The device of claim 4 further comprising means for providing a refractory period between selected ones of said at least one pulse.

8. The device of claim 4 further comprising means for varying the pulse width of each of said at least one pulse to selected widths.

* * * * *